United States Patent
Paget et al.

(10) Patent No.: US 6,951,863 B2
(45) Date of Patent: Oct. 4, 2005

(54) PYRIDOARYLPHENLY OXAZOLIDINONE ANTIBACTERIALS, AND RELATED COMPOSITIONS AND METHODS

(75) Inventors: Steven D. Paget, Hillsborough, NJ (US); Michele A. Weidner-Wells, Hillsborough, NJ (US); Harvey M. Werblood, Piscataway, NJ (US)

(73) Assignee: Ortho-McNeil Pharmaceutical, Inc., Raritan, NJ (US)

( * ) Notice: Subject to any disclaimer, the term of this patent is extended or adjusted under 35 U.S.C. 154(b) by 274 days.

(21) Appl. No.: 10/072,534

(22) Filed: Feb. 6, 2002

(65) Prior Publication Data

US 2003/0176422 A1 Sep. 18, 2003

Related U.S. Application Data

(60) Provisional application No. 60/266,938, filed on Feb. 7, 2001.

(51) Int. Cl.[7] ............... A61K 31/495; A61K 31/44; A61P 11/00; C07D 471/00; C07D 491/00
(52) U.S. Cl. ............... 514/255.05; 514/249; 514/264.1; 514/292; 514/300; 514/301; 514/302; 514/303; 514/307; 544/279; 544/350; 546/81; 546/88; 546/112; 546/114; 546/115; 546/118; 546/119; 546/122; 546/144
(58) Field of Search ............... 514/249, 255.05, 514/292, 300, 301, 302, 303, 307, 264.1; 544/279, 350; 546/81, 88, 112, 114, 115, 118, 119, 122, 144

(56) References Cited

U.S. PATENT DOCUMENTS

| | | | |
|---|---|---|---|
| 5,037,834 A | 8/1991 | Brighty et al. | 514/292 |
| 5,312,823 A | 5/1994 | Petersen et al. | 514/300 |
| 5,371,090 A | 12/1994 | Petersen et al. | 514/300 |
| 5,654,428 A | 8/1997 | Barbachyn et al. | 544/235 |
| 5,792,765 A | 8/1998 | Riedl et al. | 514/236.8 |
| 5,910,504 A | 6/1999 | Hutchinson | 514/376 |

FOREIGN PATENT DOCUMENTS

| | | |
|---|---|---|
| EP | 0520277 A2 | 6/1992 |
| JP | 11322729 A | 11/1999 |
| WO | WO 93/09103 A1 | 5/1993 |
| WO | WO 95/07271 A1 | 3/1995 |
| WO | WO 95/25106 A1 | 9/1995 |
| WO | WO 96/13502 A1 | 5/1996 |
| WO | WO 9710223 A | 3/1997 |
| WO | WO 98/54161 A1 | 12/1998 |
| WO | WO 99/64416 A2 | 12/1999 |
| WO | WO 9984417 A | 12/1999 |

OTHER PUBLICATIONS

Patent Abstracts of Japan, vol. 2000, no. 2, Feb. 29, 2000.
PCT International Search Report, PCT/US02/03982, Sep. 20, 2002.
Iyer, S. et al.: "Regiospecific Synthesis of 2–Methoxy–3–methyl–1,4–benzoquinones from Maleoyl-cobalt Complexes and Alkynes via Lewis Acid Catalysis. A Highly Convergent Route to Isoquinoline Quinones." J. Am. Chem. Soc. 1987, 109, pp. 2759–2770.
Kamal, M.R. et al.; "The Chemistry of Pyrazine and its Derivatives. VII. The Synthesis of Vinyl–pyrazine and Substituted Vinylpyrazines." The J. of Org. Chem, 1962, vol. 27, pp. 1363–1366.
Piera, F. et al.: "Synthesis of Substituted Pyrazines Derived From Pyrazincarboxaldehyde and Hydroxmethylpyrazine." Anales de Quimica, 1979, vol. 75, pp. 899–903.
Sahu, D.P.; "A practical synthesis of 7–ethyl–octahydro–2–methyl–6H–pyrazino–[1,2–c] pyrimidin–6–one(Centperazine), an anti–filarial drug." Indian J. of Chem., Sec. B, 1998, pp. 1149–1152.

*Primary Examiner*—Brenda Coleman
(74) *Attorney, Agent, or Firm*—Thomas Dodd

(57) ABSTRACT

Pyridoarylphenyl oxazolidinone compounds of the formula:

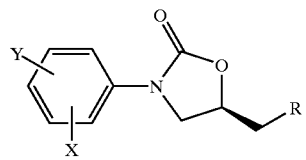

in which the substituents have the meaning indicated in the description. These compounds are useful as antibacterial agents.

22 Claims, No Drawings

PYRIDOARYLPHENLY OXAZOLIDINONE ANTIBACTERIALS, AND RELATED COMPOSITIONS AND METHODS

This application claims the benefit of U.S. Provisional Application No. 60/266,938 filed on Feb. 7, 2001, which is incorporated herein in its entirety by reference.

FIELD OF THE INVENTION

The present invention relates to the field of phenyl oxazolidinone compounds having antibacterial activity against Gram-positive and Gram-negative bacteria, pharmaceutical compositions containing the compounds, and methods of treating bacterial infections with the compounds.

BACKGROUND OF THE INVENTION

Oxazolidinones have been identified, within the last twenty years, as a new class of antibacterials which are active against numerous multidrug-resistant Gram-positive organisms. Particularly problematic pathogens include methicillin-resistant *Staphylococcus aureus* (MRSA), glycopeptide-intermediate resistant *Staphylococcus aureus* (GISA), vancomycin-resistant enterocci (VRE) and penicillin- and cephalosporin-resistant *Streptococcus pneumoniae*. As a class, oxazolidinones exhibit a unique mechanism of action. Studies have shown that these compounds selectively bind to the 50S ribosomal subunit and inhibit bacterial translation at the initiation phase of protein synthesis. Exemplary members of oxazolidinones are linezolid (see WO 95/07271) and eperezolid.

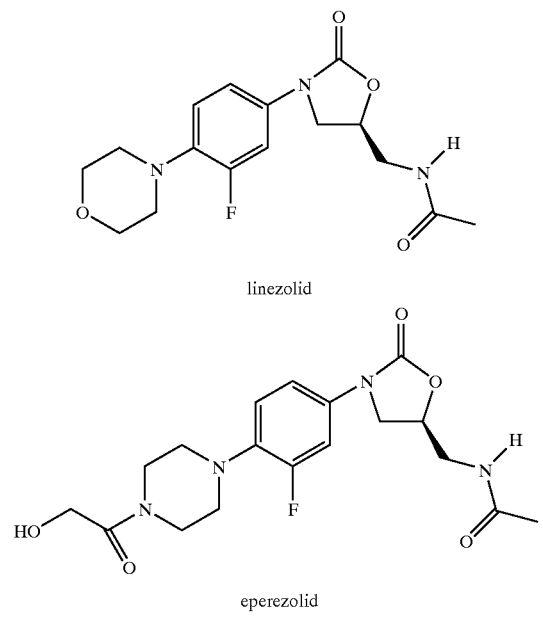

linezolid eperezolid

U.S. Pat. No. 5,792,765 to Riedl et al. discloses a series of substituted oxazolidinones (cyanoguanidine, cyanoamidines, and amidines) useful as antibacterial medicaments.

U.S. Pat. No. 5,910,504 to Hutchinson discloses a series of heteroaromatic ring substituted phenyl oxazolidinones, including indolyl substituted compounds useful as antibacterial agents.

WO 98/54161 (Hester et al.) discloses amides, thioamides, ureas, and thioureas which are antibacterial agents.

WO 95/07271 (Barbachyn et al.) discloses oxazine and thiazine oxazolidinone derivatives such as linezolid and its analogs which are useful antimicrobial agents, effective against a number of human and veterinary pathogens, including Gram-positive aerobic bacteria such as multiply-resistant staphylococci, streptococci and enterococci as well as anaerobic organisms such as *Bacteroides* spp. and *Clostridia* spp., and acid-fast organisms such as *Mycobacterium tuberculosis, Mycobacterium avium* and *Mycobacterium* spp.

WO 93/09103 (Barbachyn et al.) discloses substituted aryl- and heteroarylphenyloxazolidinones that are useful as antibacterial agents.

SUMMARY OF THE INVENTION

The invention provides pyridoarylphenyl oxazolidinone compounds of Formula I

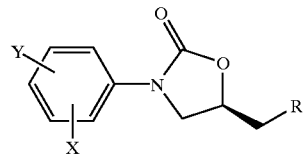

Formula I wherein:
R is selected from the group consisting of OH, $N_3$, —$OR_1$, —O-aryl, —O-heteroaryl, —$OSO_2R_2$, —$NR_3R_4$, and

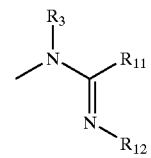

wherein
(i) $R_1$ is benzyl or $C_{2-6}$-acyl;
(ii) $R_2$ is selected from the group consisting of phenyl, tolyl, and $C_{1-8}$-alkyl; and
(iii) $R_3$ and $R_4$ are independently selected from the group consisting of hydrogen, $C_{3-6}$-cycloalkyl, phenyl, tert-butoxycarbonyl, fluorenyloxycarbonyl, benzyloxycarbonyl, —$CO_2$—$R_5$, —CO—$R_5$, —CO—$SR_5$, —CS—$R_5$, P(O)($OR_6$)($OR_7$), —$SO_2$—$R_8$ and $C_{1-6}$-alkyl optionally substituted with 1 to 3 members independently selected from the group consisting of $C_{1-5}$-alkoxycarbonyl, OH, cyano, and halogen, wherein $R_5$ is selected from the group consisting of hydrogen, $C_{3-6}$-cycloalkyl, trifluoromethyl, phenyl, benzyl, and $C_{1-6}$-alkyl optionally substituted with 1 to 3 members independently selected from the group consisting of $C_{1-5}$-alkoxycarbonyl, OH, cyano, halogen, and —$NR_9R_{10}$ in which $R_9$ and $R_{10}$ are independently selected from the group consisting of hydrogen, phenyl and $C_{1-4}$-alkyl;
$R_6$ and $R_7$ are independently hydrogen or $C_{1-4}$-alkyl; and
$R_8$ is phenyl or $C_{1-4}$-alkyl;
$R_{11}$ is selected from the group consisting of hydrogen, alkyl, —$OR_{13}$, —$SR_{13}$, amino, —$NR_{13}R_{14}$, aryl ($C_{1-8}$)alkyl, and mono-, di-, tri-, or per-halo $C_{1-8}$-alkyl;
$R_{12}$ is selected from the group consisting of CN, —$COR_{13}$, —$COOR_{13}$, —CO—$NR_{13}R_{14}$, —$SO_2R_{13}$, —$SO_2$—$NR_{13}R_{14}$, and nitro; and $R_{13}$ and $R_{14}$ are independently selected from the group consisting of hydrogen, alkyl, and aryl, or $R_{13}$ and $R_{14}$ taken together with the nitrogen atom to which they are attached form an unsubstituted or substituted pyrrolidinyl, piperidinyl morpholinyl, thiomorpholinyl, or piperazinyl group;

X is 0 to 4 members independently selected from the group consisting of halogen, OH, mercapto, nitro, , $C_{1-8}$-alkoxy, $C_{1-8}$-alkylthio, $C_{1-8}$-alkyl-amino, di($C_{1-8}$-alkyl)amino, formyl, carboxy, alkoxycarbonyl, $C_{1-8}$alkyl-CO—O—, $C_{1-8}$alkyl-CO—NH—, carboxamide, aryl, heteroaryl, CN, amino, $C_{3-6}$-cycloalkyl, $C_{1-8}$-alkyl optionally substituted with one or more members selected from the group consisting of F, Cl, OH, $C_{1-8}$ alkoxy and $C_{1-8}$ acyloxy; and Y is a radical of Formula II:

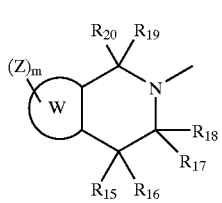

Formula II wherein $R_{15}$, $R_{16}$, $R_{17}$, $R_{18}$, $R_{19}$, and $R_{20}$ are each independently selected from the group consisting of hydrogen, CN, nitro, $C_{1-8}$-alkyl, halo-$C_{1-8}$-alkyl, formyl, carboxy, alkoxycarbonyl, carboxamide, aryl, and heteroaryl, or $R_{15}$ and $R_{16}$ and/or $R_{17}$ and $R_{18}$ and/or $R_{19}$ and $R_{20}$ together form an oxo group;

the moiety W represents any five- to ten-membered aromatic or heteroaromatic ring, said heteroaromatic ring having 1 to 4 members selected from the group consisting of S, O, and N;

Z is selected from the group consisting of hydrogen, halogen, amino, alkyl, cycloalkyl, aryl, heteroaryl, heterocyclyl, CN, CHO, alkyl-CO—, alkoxy, ($C_{1-8}$-alkyl)-CONH—, and $R_{21}R_{22}$N-alkyl-wherein $R_{21}$ and $R_{22}$ are independently selected from the group consisting of hydrogen, $C_{1-6}$-alkyl, benzyl, aryl, and heteroaryl, or $R_{21}$ and $R_{22}$ together with the nitrogen to which they are attached form an unsubstituted or substituted pyrrolidinyl, piperidinyl, morpholinyl, thiomorpholinyl, or piperazinyl group; and m is 0 or 1 and the pharmaceutically acceptable salts and esters thereof.

Preferably, the moiety W is a fused phenyl ring or a five- or six-membered heteroaromatic ring having 1 to 4 members selected from the group consisting of S, O, and N.

For the radical Y the following heterocycles are particularly preferred, wherein Z is selected from the group consisting of hydrogen, alkyl, aryl, heteroaryl, alkyl-CO—, and $R_{21}R_{22}$N-alkyl- wherein $R_{21}$ and $R_{22}$ are independently selected from the group consisting of hydrogen, $C_{1-6}$-alkyl, benzyl, aryl, and heteroaryl, or $R_{21}$ and $R_{22}$ together with the nitrogen to which they are attached form an unsubstituted or substituted pyrrolidinyl, piperidinyl, morpholinyl, thiomorpholinyl, or piperazinyl group:

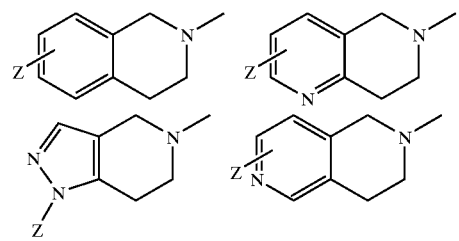

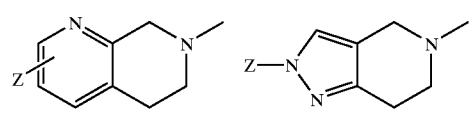

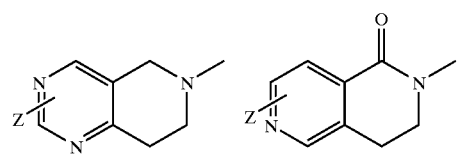

Compounds of the present invention are useful as antibacterial agents for the treatment of bacterial infections in humans and animals.

The present invention is also directed to a method of treating a subject having a condition caused by or contributed to by bacterial infection, which comprises administering to said mammal a therapeutically effective amount of the compound of Formula I.

The present invention is further directed to a method of preventing a subject from suffering from a condition caused by or contributed to by bacterial infection, which comprises administering to the subject a prophylactically effective dose of the pharmaceutical composition of a compound of Formula I.

Other objects and advantages will become apparent to those skilled in the art from a review of the ensuing specification.

DETAILED DESCRIPTION

Relative to the above description of the pyridoarylphenyl oxazolidinone compounds of the present invention, the following definitions apply.

Unless otherwise noted, under standard nomenclature used throughout this disclosure the terminal portion of the designated side chain is described first, followed by the adjacent functionality toward the point of attachment.

Unless specified otherwise, the terms "alkyl", "alkenyl", and "alkynyl" may be straight or branched groups with 1–8 carbon atoms. Unless noted otherwise, "alkyl", "alkenyl", and "alkynyl" may have one or more substituents selected from amino, dialkylamino, cycloalkyl, hydroxy, oxo, alkoxycarbonyl, benzyloxy, arylthio, alkylthio, hydroxyalkylthio, alkylsulfinyl, alkylsulfonyl, carboxy, phosphonooxy, dialkylphosphonooxy, dibenzylphosphonooxy, cyano, halo, trialkylsilyl, dialkylphenylsilyl, aryl, heteroaryl, heterocyclo, heterocyclomethylbenzoyloxy, dialkylaminomethylbenzoyloxy, dialkylaminoalkylcarbonyloxy, benzyloxycarbonylaminoalkylcarbonyloxy, and aminoalkylcarbonyloxy.

"Acyl" means an organic radical having the designated number of carbon atoms, derived from an organic acid by the removal of a hydroxyl group having the formula RCO wherein R is alkyl, as in the case of acetyl where R is $CH_3$.

"Aryl" is a carbocyclic aromatic group including, but not limited to, phenyl, 1- or 2-naphthyl and the like. "Heteroaryl" refers to a cyclic aromatic radical having from five to ten atoms in the ring; where one to three ring atoms are independent heteroatoms such as S, O, and N, and the remaining ring atoms are carbon, for example, a pyridinyl, pyrazinyl, pyrimidinyl, pyrroyl, pyrazolyl, imidazolyl, thiazolyl, oxazolyl, isoxazolyl, thiadiazolyl, oxadiazolyl, thienyl, furanyl, quinolinyl, or isoquinolinyl radical and the like.

Unless specified otherwise, "aryl" or "heteroaryl" may be substituted by independent replacement of 1–3 of the hydrogen atoms thereon with halogen, OH, CN, mercapto, nitro, $C_{1-8}$-alkyl, halo-$C_{1-8}$-alkyl, $C_{1-8}$-alkoxy, $C_{1-8}$-alkylthio, amino, $C_{1-8}$-alkyl-amino, di($C_1$-$C_8$-alkyl-)amino, formyl, carboxy, alkoxycarbonyl, $C_{1-8}$-alkyl-CO—O—, $C_{1-8}$-alkyl-CO—NH—, or carboxamide. Further, substituted heteroaryl may be substituted with a mono-oxo to give, for example, a 4-oxo-1-H-quinoline. Substituted heteroaryl may also be substituted with a substituted aryl or a second substituted heteroaryl to give, for example, a 2-phenylpyrimidine or a 2-(pyrid-4-yl)pyrimidine, and the like.

The term "halo" or "halogen" means fluoro, chloro, bromo and iodo. (Mono-, di-, tri-, and per-) halo-alkyl is an alkyl radical substituted by independent replacement of the hydrogen atoms thereon with halogen. P denotes phosphorus.

The compounds of the instant invention are asymmetric in the oxazolidinone ring at the 5-position and thus exist as optical antipodes. As such, all possible optical antipodes, enantiomers or diastereomers resulting from additional asymmetric centers that may exist in optical antipodes, racemates and racemic mixtures thereof are also part of this invention. The antipodes can be separated by methods known to those skilled in the art such as, for example, fractional recrystallization of diastereomeric salts of enantiomerically pure acids. Alternatively, the antipodes can be separated by chromatography on a Pirkle column.

The phrase "pharmaceutically acceptable salts" denotes salts of the free base which possess the desired pharmacological activity of the free base and which are neither biologically nor otherwise undesirable. These salts may be derived from inorganic or organic acids. Examples of inorganic acids are hydrochloric acid, nitric acid, hydrobromic acid, sulfuric acid, or phosphoric acid. Examples of organic acids are acetic acid, propionic acid, glycolic acid, lactic acid, pyruvic acid, malonic acid, succinic acid, malic acid, maleic acid, fumaric acid, tartaric acid, citric acid, benzoic acid, cinnamic acid, mandelic acid, methanesulfonic acid, ethanesulfonic acid, p-toluenesulfonic acid, salicyclic acid and the like. Suitable salts are furthermore those of inorganic or organic bases, such as KOH, NaOH, $Ca(OH)_2$, $Al(OH)_3$, piperidine, morpholine, ethylamine, triethylamine and the like.

Also included within the scope of the invention are the hydrated forms of the compounds that contain various amounts of water, for instance, the hydrate, hemihydrate and sesquihydrate forms.

The term "subject" includes, without limitation, any animal or artificially modified animal. In the preferred embodiment, the subject is a human.

The term "drug-resistant" or "drug-resistance" refers to the characteristics of a microbe to survive in the presence of a currently available antimicrobial agent at its routine, effective concentration.

The compounds of the present invention possess antibacterial activity against Gram-positive and certain Gram-negative bacteria. They are useful as antibacterial agents for the treatment of bacterial infections in humans and animals. Particularly, these compounds have antimicrobial activity against S. aureus, S. epidermidis, S. pneumoniae, E. faecalis, E. faecium, Moraxella catarrhalis, and H. influenzae. More particularly, these compounds are useful against resistant bacteria such as MRSA and GISA, and have a low susceptibility to acquired resistance mechanisms. Compounds of Formula I most preferred for such purposes are those in which R is any of the following:

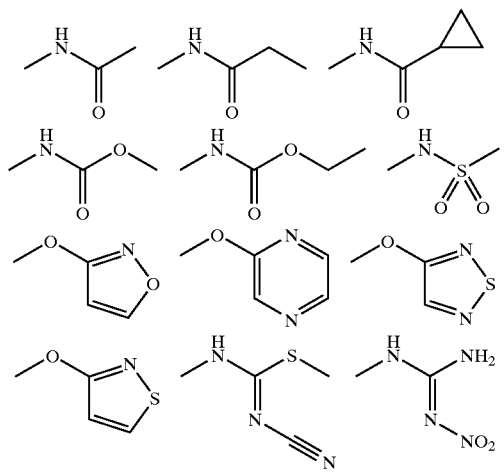

In addition, compounds of Formula I which are most preferred for such purposes are those in which Y is any of the following, wherein Z is selected from the group consisting of hydrogen, alkyl, aryl, heteroaryl, alkyl-CO—, and $R_{21}R_{22}$N-alkyl- wherein $R_{21}$ and $R_{22}$ are independently selected from the group consisting of hydrogen, $C_{1-6}$-alkyl, benzyl, aryl, and heteroaryl, or $R_{21}$ and $R_{22}$ together with the nitrogen atom to which they are attached form a pyrrolidinyl, piperidinyl, morpholinyl, thiomorpholinyl, or piperazinyl group:

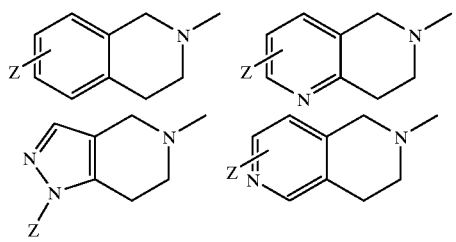

-continued

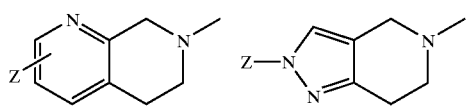

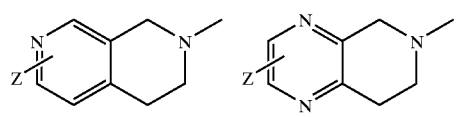

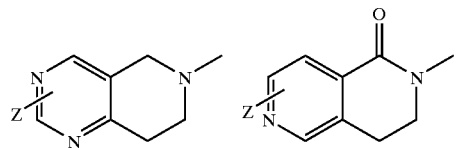

Particular examples of the present invention include the following compounds:

Compound 1: 2-oxazolidinone, 3-[4-(3,4-dihydro-2 (1H)-isoquinolinyl)-3-fluorophenyl]-5-(hydroxymethyl)-, (5R)-;

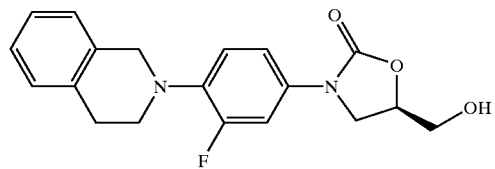

Compound 2: acetamide, N-[[(5S)-3-[4-(3,4-dihydro-2(1H)-isoquinolinyl)-3-fluorophenyl]-2-oxo-5-oxazolidinyl]methyl]-

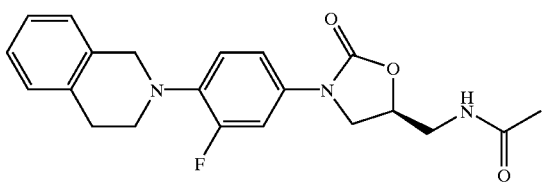

Compound 3: acetamide, N-[[(5S)-3-[4-(3,4-dihydro-2,7-naphthyridin-2(1H)-yl)-3-fluorophenyl]-2-oxo-5-oxazolidinyl]methyl]-

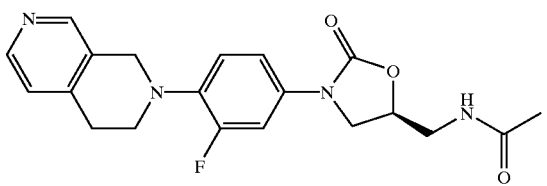

Compound 4: acetamide, N-[[(5S)-3-[4-(3,4-dihydro-1-oxo-2,6-naphthyridin-2(1H)-yl)-3-fluorophenyl]-2-oxo-5-oxazolidinyl]methyl]-

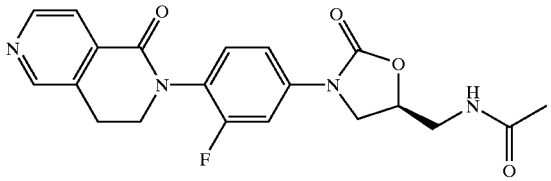

Compound 5: acetamide, N-[[(5S)-3-[4-(7,8-dihydropyrido[4,3-d]pyrimidin-6(5H)-yl)-3-fluorophenyl]-2-oxo-5-oxazolidinyl]methyl]-

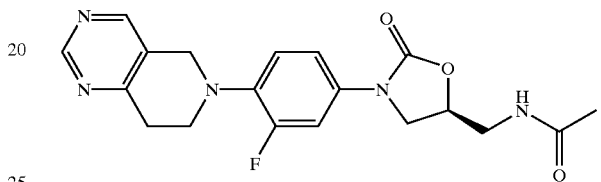

Compound 6: acetamide, N-[[(5S)-3-[4-(7,8-dihydro-2-methylpyrido[4,3-d]pyrimidin-6(5H)-yl)-3-fluorophenyl]-2-oxo-5-oxazolidinyl]methyl]-

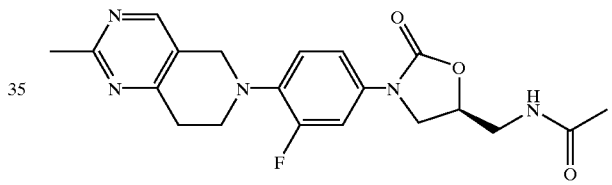

Compound 7: acetamide, N-[[(5S)-3-[4-[7,8-dihydro-2-(2-methyl-4-thiazolyl)pyrido[4,3-d]pyrimidin-6(5H)-yl]-3-fluorophenyl]-2-oxo-5-oxazolidinyl]methyl]-

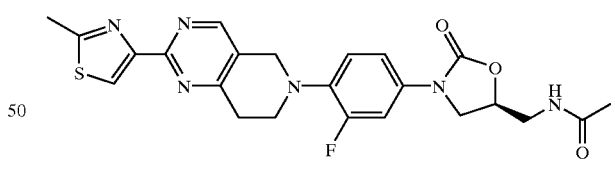

Compound 8: acetamide, N-[[(5S)-3-[4-[7,8-dihydro-2-(4-pyridinyl)pyrido[4,3-d]pyrimidin-6(5H)-yl]-3-fluorophenyl]-2-oxo-5-oxazolidinyl]methyl]-

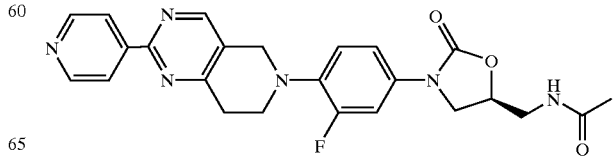

Compound 9: acetamide, N-[[(5S)-3-[4-(7,8-dihydro-2-pyrazinylpyrido[4,3-d]pyrimidin-6(5H)-yl)-3-fluorophenyl]-2-oxo-5-oxazolidinyl]methyl]-

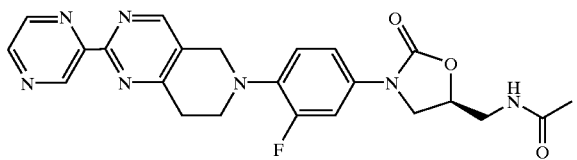

Compound 11: acetamide, N-[[(5S)-3-[4-(1,4,6,7-tetrahydro-1-methyl-5H-pyrazolo[4,3-c]pyridin-5-yl)-3-fluorophenyl]-2-oxo-5-oxazolidinyl]methyl]-

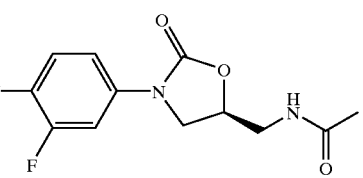

Compound 10: acetamide, N-[[(5S)-3-[4-(1,4,6,7-tetrahydro-5H-pyrazolo[4,3-c]pyridin-5-yl)-3-fluorophenyl]-2-oxo-5-oxazolidinyl]methyl]-

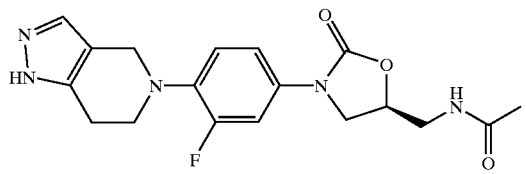

The compounds of Formula I that are the subject of this invention may be prepared from readily available starting materials, such as tetrahydroisoquinoline (Aldrich Chemical Co), and in accordance with synthetic methods well known in the art. Representative procedures are outlined in Schemes I–VI:

Scheme I

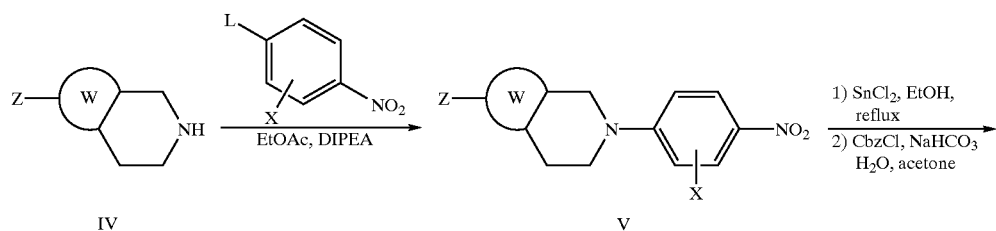

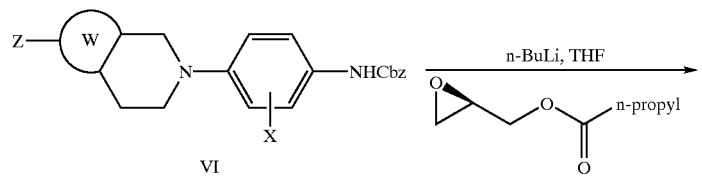

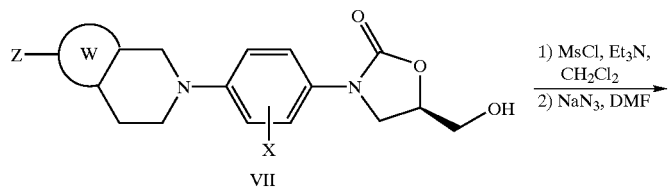

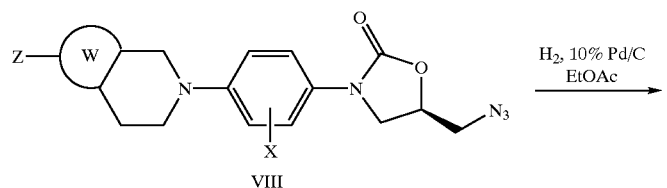

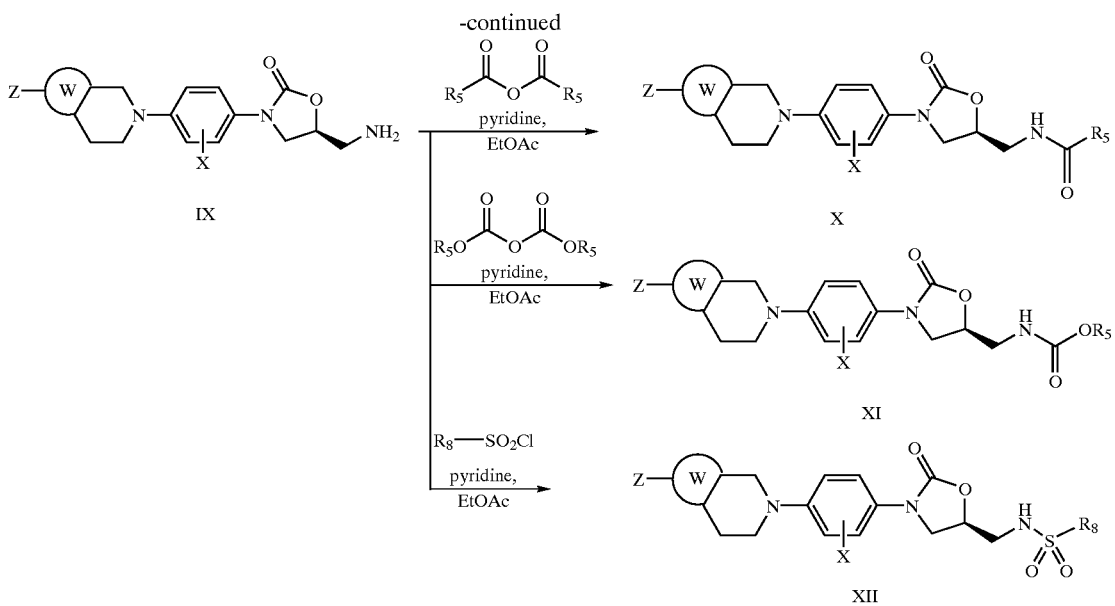

In accordance with Scheme I, bicyclic heterocycles of general formula IV are treated with a substituted nitrobenzene derivative (L is an appropriate leaving group such as a halogen or trifluoromethanesulfonyloxy) in a suitable base and solvent, such as diisopropylamine and ethyl acetate, to give the substituted nitrophenyl compound V. The nitrobenzene derivative V is then reduced to the aniline by an appropriate reaction, for instance by treatment with tin (II) chloride or by catalytic hydrogenation in the presence of a suitable catalyst such as palladium on carbon. The aniline is then treated with benzyl or methyl chloroformate and sodium bicarbonate to form the corresponding benzyl or methyl carbamate derivative VI. The Cbz aniline derivative VI can be deprotonated with a lithium base such as n-butyllithium and reacted with (R)-glycidyl butyrate to afford the oxazolidinone VII. The hydroxymethyl group can then be converted to an amide by preparation of the mesylate, conversion to azide VIII, and reduction to amine IX by an appropriate procedure such as hydrogenation. Alternatively displacement of a mesylate (Scheme II) or appropriate leaving group such as tosylate or chloride with potassium phthalimide and removal of the phthaloyl protecting group by hydrazinolysis would provide amine IX.

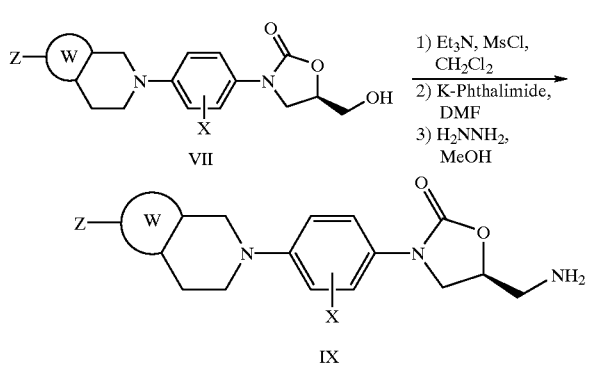

Finally, the amine IX can be converted to amide X by an acylation reaction using techniques known in the art, such as treatment with acetic anhydride in the presence of a base such as pyridine. Amine IX can also be converted to a carbamate XI by treatment with a suitable chloroformate or pyrocarbonate derivative and pyridine, or reacted with a sulfonyl chloride in an inert solvent in the presence of an organic base like pyridine to form a sulfonamide XII.

Scheme III

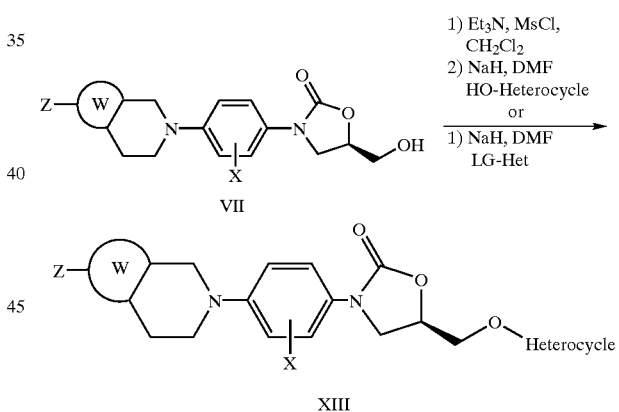

For the formation of an oxazolidinone in which R is O-heteroaryl (XIII), the oxazolidinone carbinol VII can be converted to the corresponding mesylate or other appropriate leaving group and reacted with HO-Het (a suitable hydroxyl containing heterocycle), either in the presence of base or with HO-Het as a preformed alkoxide, in an appropriate solvent, for example DMF or acetonitrile (Scheme III). Alternatively, Mitsunobu conditions can be used to couple VII with HO-heterocycle by treating, for example, with triphenylphosphine and diisopropyl azodicarboxylate (DIAD) in an appropriate solvent, such as THF, at a suitable temperature (preferably room temperature). Reaction conditions and leading references can be found in Gravestock et al. WO 99/64416.

Also shown in Scheme II, formation of an oxazolidinone in which R is O-heteroaryl (XIII) can also be effected by nucleophilic displacement of a leaving group (LG), such as chlorine or bromine, from an appropriately reactive aza-heterocycle (LG-Het) with the alkoxide derived from VII by deprotonation with a suitable, non-nucleophilic base (for example NaH).

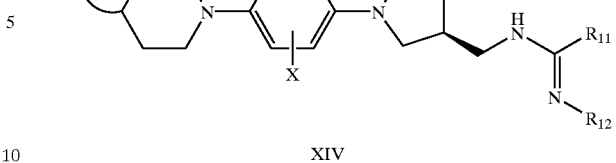

XIV

Compounds of structure XIV can be prepared as shown in Scheme IV. Amine IX can be converted to various functionalized amidines by reaction with activated imines, where Q is a leaving group such as methylthio or methoxy, in a suitable solvent, for example toluene or methanol, with or without a catalyst (such $AgNO_3$) at a temperature preferably between 0–110° C.

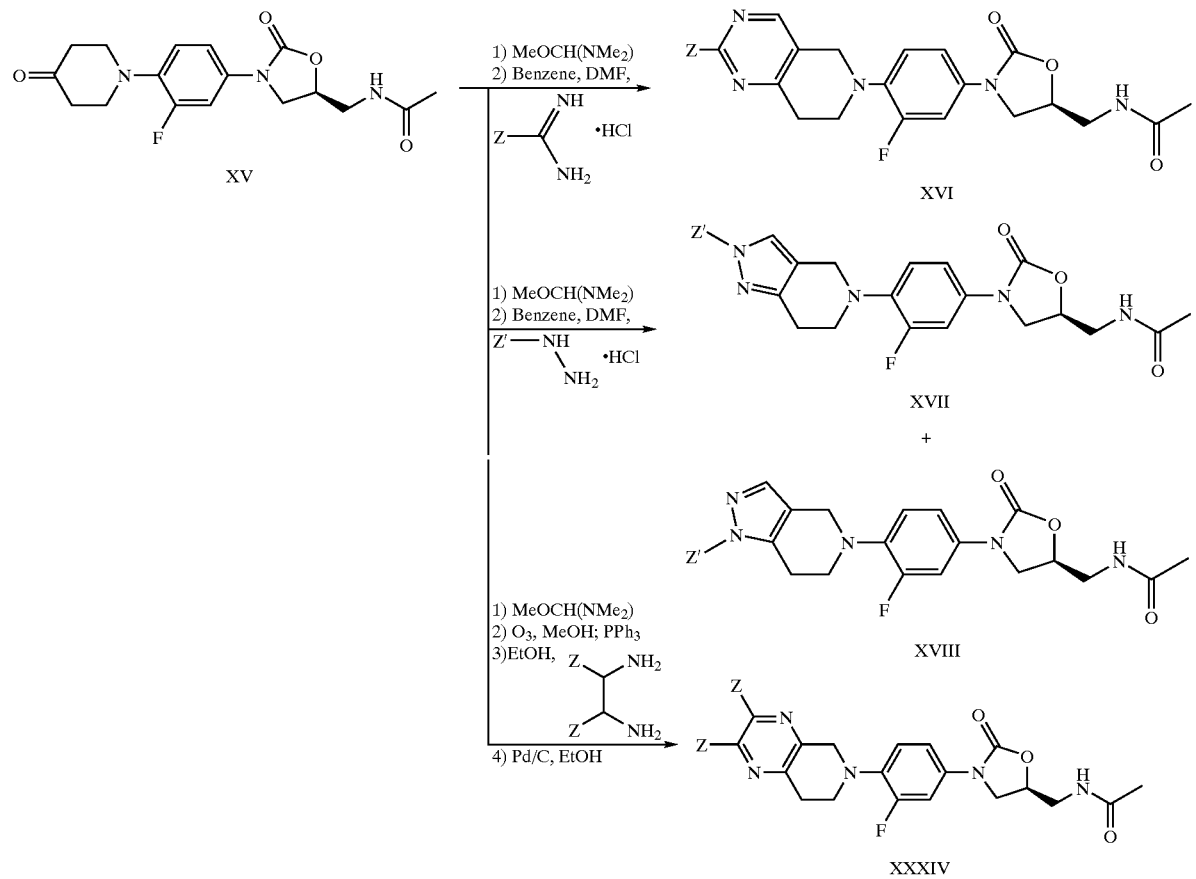

In accordance with Scheme V, phenylpiperidinone XV (prepared as in WO 95/25106 and WO 96/13502) is first reacted with methoxy-bis(dimethylamine) or other formylating reagent and, second, heated in a suitable solvent (for example DMF and benzene) with either a substituted amidine, to form pyridopyrimidinylphenyl oxazolidinones such as XVI, or a substituted hydrazine, to form pyridopyrazolylphenyl oxazolidinones such as XVII and XVIII, wherein Z' is selected from hydrogen, alkyl, aryl, heteroaryl, alkyl-CO—, and $R_{21}R_{22}N$-alkyl- wherein $R_{21}$ and $R_{22}$ are independently selected from the group consisting of hydrogen, $C_{1-6}$-alkyl, benzyl, aryl, and heteroaryl, or $R_{21}$ and $R_{22}$ together with the nitrogen atom to which they are attched form an unsubstituted or substituted pyrrolidinyl, piperidinyl, morpholinyl, thiomorpholinyl, or piperazinyl group. Formation of the β-enamine, alkoxymethylene or alkoxycarbonyl derivatives of phenylpiperidinone XV, according to Brighty et al. in U.S. Pat. No. 5,037,834, also allows access to these heterocyclic ring systems. Ozonolysis of the previously generated β-enamine intermediate followed by triphenylphosphine work-up and subsequent reaction with a diamine would allow, after aromatization with palladium on carbon, access to pyridopyrazine oxazolidinones (such as XXXIV).

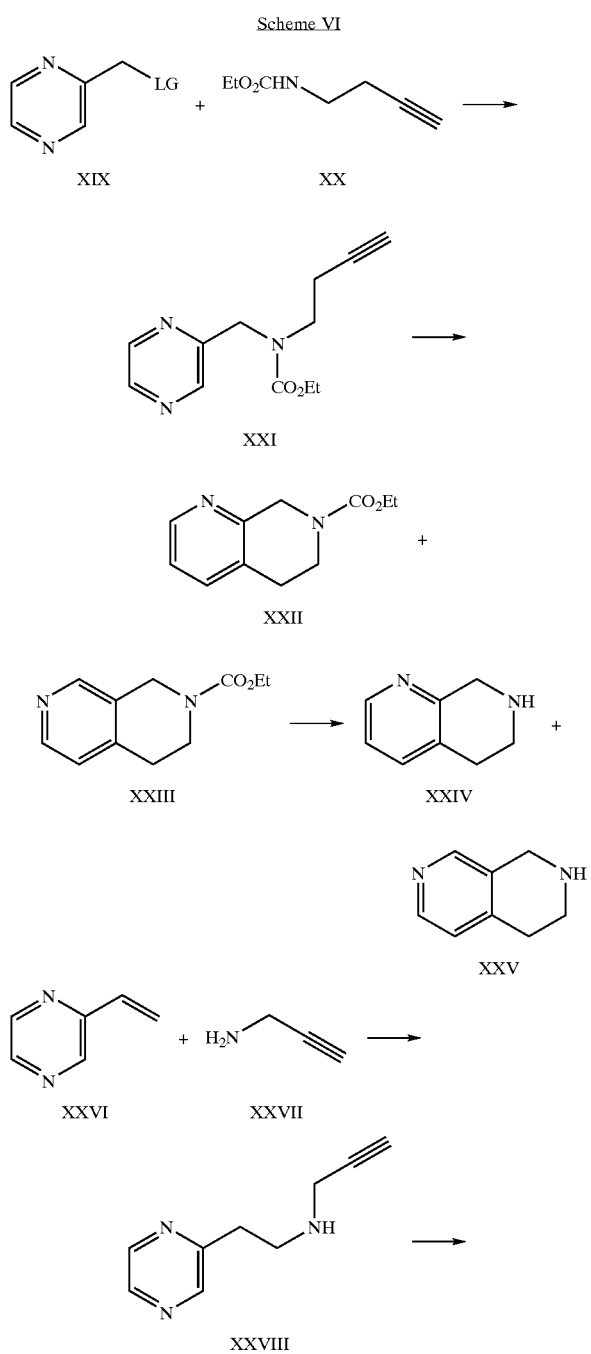

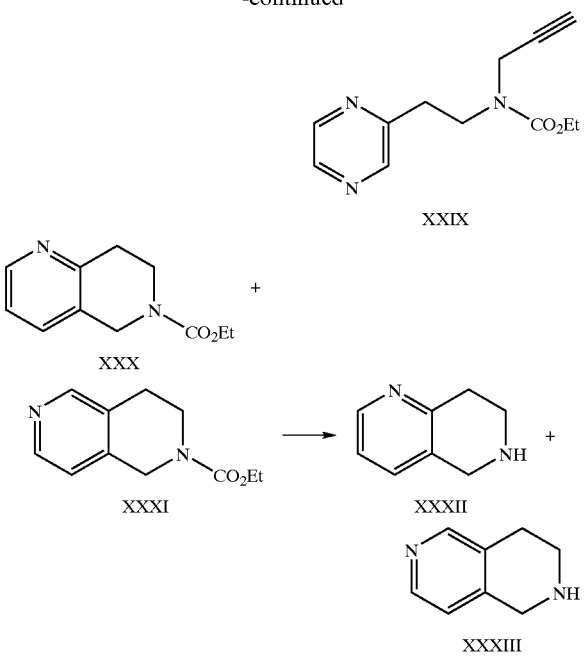

Access to various isomeric pyridopyridines can be achieved as shown in Scheme VI. Methyl pyrazine, substituted with an appropriate leaving group (XIX) such as chlorine or methanesulfonyloxy, can be reacted with the ethyl carbamate derivative of homopropargylamine (XX) under basic conditions to provide an intermediate such as XXI. Upon heating XXI under acidic (such as trifluoroacetic acid) or neutral (such as undecane or other high boiling organic solvents) conditions a cycloaddition/extrusion reaction occurs to provide pyrido[3,4-b]pyridine derivative (XXII) and pyrido[3,4-c]pyridine derivative (XXIII) (following procedures outlined in EP 0520277 to Petersen et al.). Removal of the ethyl carbamate functionality can be readily effected by treatment with acid, such as hydrochloric acid at reflux temperature to give the corresponding secondary amine derivatives (XXIV and XXV). The other complementary isomers are accessed by reacting vinyl pyrazine (XXVI) with propargyl amine (XXVII) with subsequent protection of the amine (XXVIII) as its ethyl carbamate derivative (XXIX) (in the manner of Sahu, *Indian J. Chem. Sec. B: Org. Chem. Incl. Med. Chem.* 1998, 37, 1149). Similar to the sequence described above, heating XXIX under acidic or neutral conditions provides the pyrido[4,3-b]pyridine derivative (XXX) and the pyrido[4,3-c]pyridine derivative (XXXI). Removal of the ethyl carbamate functionality can be readily effected by treatment with acid, such as hydrochloric acid at reflux temperature to give the corresponding secondary amine derivatives (XXXII and XXXIII).

Definitions:
  All temperatures are in degrees Centigrade
  Brine refers to an aqueous saturated sodium chloride solution
  DMF refers to N,N-dimethylformamide
  THF refers to tetrahydrofuran
  Cbz refers to carbobenzyloxy
  n-BuLi refers to n-butyl lithium
  MS refers to mass spectrometry expressed as m/e or mass/charge unit
  [M+1] refers to the positive ion of a parent plus a hydrogen atom Ether refers to diethyl ether
rt refers to room temperature
mp refers to melting point
$CH_2Cl_2$ refers to methylene chloride
NaOH refers to sodium hydroxide
MeOH refers to methanol
EtOAc refers to ethyl acetate
ppt refers to a precipitate These compounds have antimicrobial activity against susceptible and drug resistant bacterial pathogens such as *S. aureus, S. epidermidis, S. pneumoniae, S. pyogenes, Enterococcus* spp., *Moraxella catarrhalis* and *H. influenzae*. These compounds are particularly useful against drug resistant Gram-positive cocci such as methicillin-resistant *S. aureus* and vancomycin-resistant enterococci. These compounds are useful in the treatment of community-acquired pneumonia, upper and lower respiratory tract infections, skin and soft tissue infections, hospital-acquired lung infections, bone and joint infections, and other bacterial infections.

Minimal inhibitory concentration (MIC) has been an indicator of in vitro antibacterial activity widely used in the art. The in vitro antimicrobial activity of the compounds was determined by the microdilution broth method following the test method from the National Committee for Laboratory Standards (NCCLS). This method is described in the NCCLS Document M7-A4, Vol. 17, No. 2, "Methods for Dilution Antimicrobial Susceptibility Test for Bacteria that Grow Aerobically—Fourth Edition", which is incorporated herein by reference.

In this method two-fold serial dilutions of drug in cation adjusted Mueller-Hinton broth are added to wells in microdilution trays. The test organisms are prepared by adjusting the turbidity of actively growing broth cultures so that the final concentration of test organism after it is added to the wells is approximately $5 \times 10^4$ CFU/well.

Following inoculation of the microdilution trays, the trays are incubated at 35° C. for 16–20 hours and then read. The MIC is the lowest concentration of test compound that completely inhibits growth of the test organism. The amount of growth in the wells containing the test compound is compared with the amount of growth in the growth-control wells (no test compound) used in each tray. As set forth in Table 1, some compounds of the present invention were tested against a variety of pathogenic bacteria resulting in a range of activities, from 1 to >128 μg/mL depending on the organism tested. *S. aureus* OC2878 is a MRSA and *E. faecium* OC3312 is a vancomycin-resistant enterococcus.

TABLE 1

MIC Values of Some Compounds of Formula I

| Compound No. | MIC (μg/mL) in Test Strains | | |
| --- | --- | --- | --- |
| | *S. aureus* OC4172 | *S. aureus* OC2878 | *E. faecium* OC3312 |
| 1 | 128 | 32 | >128 |
| 2 | 8 | 4 | 8 |
| 3 | 8 | 4 | 8 |
| 4 | 32 | 16 | 32 |
| 5 | 4 | 2 | 8 |
| 6 | 4 | 2 | 8 |
| 7 | 8 | 8 | 8 |
| 8 | 2 | 2 | 4 |
| 9 | 4 | 4 | 8 |
| 10 | 8 | 8 | 16 |
| 11 | 16 | 8 | 16 |

This invention further provides a method of treating bacterial infections, or enhancing or potentiating the activity of other antibacterial agents, in a subject having conditions caused by or contributed to by bacterial infection, which comprises administering to the animals a compound of the invention alone or in admixture with another antibacterial agent in the form of a medicament according to the invention. The terms "treating" and "treatment" include administering, either simultaneously, separately or sequentially, a pharmaceutically effective amount of a composition containing one or more of the compounds disclosed herein to a subject that desires inhibition of bacterial growth. The pharmaceutically effective amount of the compound used to practice the present invention for treatment varies depending on the manner of administration, the age, weight, and general health of the subject treated, and ultimately will be decided by physicians or veterinarians.

The compounds of the present invention may be administered to a subject such as a human by any route appropriate to the condition to be treated, suitable routes including oral, rectal, nasal, topical (including buccal and sublingual), vaginal and parenteral (including subcutaneous, intramuscular, intravenous, intradermal, intrathecal and epidural). The preferred route may vary with, for example, the condition of the recipient as well as the ease of preparation and administration.

When the compounds are employed for the above utility, they may be combined with one or more pharmaceutically acceptable carriers, e.g., solvents, diluents, and the like, and may be administered orally in such forms as tablets, capsules, dispersible powders, granules, or suspensions containing for example, from about 0.5% to 5% of suspending agent, syrups containing, for example, from about 10% to 50% of sugar, and elixirs containing, for example, from about 20% to 50% ethanol, and the like, or parenterally in the form of sterile injectable solutions or suspensions containing from about 0.5% to 5% suspending agent in an isotonic medium. These pharmaceutical preparations may contain, for example, from about 0.5% up to about 90% of the active ingredient in combination with the carrier, more usually between 5% and 60% by weight.

Compositions for topical application may take the form of liquids, creams or gels, containing a therapeutically effective concentration of a compound of the invention admixed with a dermatologically acceptable carrier.

In preparing the compositions in oral dosage form, any of the usual pharmaceutical media may be employed. Solid carriers include starch, lactose, dicalcium phosphate, microcrystalline cellulose, sucrose and kaolin, while liquid carriers include sterile water, polyethylene glycols, non-ionic surfactants and edible oils such as corn, peanut and sesame oils, as are appropriate to the nature of the active ingredient and the particular form of administration desired. Adjuvants customarily employed in the preparation of pharmaceutical compositions may be advantageously included, such as flavoring agents, coloring agents, preserving agents, and antioxidants, for example, vitamin E, ascorbic acid, BHT and BHA.

The preferred pharmaceutical compositions from the standpoint of ease of preparation and administration are solid compositions, particularly tablets and hard-filled or liquid-filled capsules. Oral administration of the compounds is preferred. These active compounds may also be administered parenterally or intraperitoneally. Solutions or suspensions of these active compounds as a free base or pharmacological acceptable salt can be prepared in water suitably mixed with a surfactant such as hydroxypropylcellulose. Dispersions can also be prepared in glycerol, liquid polyethylene glycols and mixtures thereof in oils. Under ordinary conditions of storage and use, these preparations may contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (e.g., glycerol, propylene glycol and liquid polyethylene glycol), suitable mixtures thereof, and vegetable oils.

The effective dosage of active ingredient employed may vary depending on the particular compound employed, the mode of administration and the severity of the condition being treated. However, in general, satisfactory results are obtained when the compounds of the invention are administered at a daily dosage of from about 0.1 mg/kg to about 400 mg/kg of animal body weight, preferably given in divided doses two to four times a day, or in sustained release form. For most large mammals the total daily dosage is from about 0.07 g to 7.0 g, preferably from about 100 mg to 2000 mg. Dosage forms suitable for internal use comprise from about 100 mg to 1000 mg of the active compound in intimate admixture with a solid or liquid pharmaceutically acceptable carrier. This dosage regimen may be adjusted to provide the optimal therapeutic response. For example, several divided doses may be administered daily or the dose may be proportionally reduced as indicated by the exigencies of the therapeutic situation.

The production of the above-mentioned pharmaceutical compositions and medicaments is carried out by any method known in the art, for example, by mixing the active ingredients(s) with the diluent(s) to form a pharmaceutical composition (e.g. a granulate) and then forming the composition into the medicament (e.g. tablets).

The following examples describe in detail the chemical synthesis of representative compounds of the present invention. The procedures are illustrations, and the invention should not be construed as being limited by chemical reactions and conditions they express. No attempt has been made to optimize the yields obtained in these reactions, and it would be obvious to one skilled in the art that variations in reaction times, temperatures, solvents, and/or reagents could increase the yields.

EXAMPLE 1

2-Oxazolidinone, 3-[4-(3,4-dihydro-2(1H)-isoquinolinyl)-3-fluorophenyl]-5-(hydroxymethyl)-, (5R)-

Compound 1

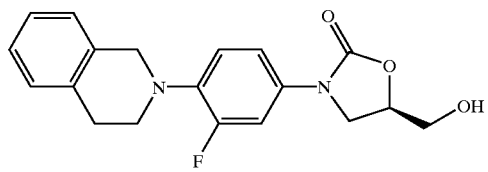

Step 1

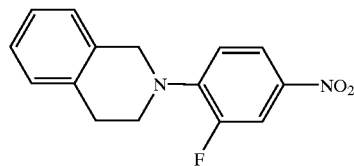

To 3,4-difluoronitrobenzene (7.96 mL, 71.2 mmol) in EtOAc (45 mL) at rt was added diisopropylethylamine (16.5 mL, 94.7 mmol) and then tetrahydroisoquinoline (10.6 mL, 83.0 mmol) and the resulting mixture stirred overnight. A yellow precipitate formed and was collected on a filter, washed with water (50 mL) and ether (30 mL) and dried in a vacuum oven (50° C.) to provide the product as a bright yellow solid (18.9 g, 84% yield). mp=107–108.5° C. MS (M+1)=273 m/z.

Step 2

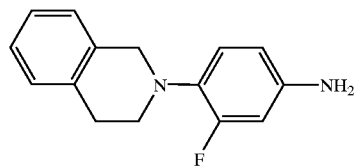

To the above nitro compound (13.1 g, 48.2 mmol) in THF (100 mL) and MeOH was added ammonium formate (14.6 g, 224 mmol) and the mixture degassed by bubbling nitrogen through the mixture for 30 min. To this mixture was added 10% palladium on carbon (0.53 g, 0.50 mmol) and, after three hours, an additional portion of ammonium formate (5.05 g, 77.7 mmol). After stirring overnight at rt the reaction mixture was filtered through Celite (washing with MeOH), reduced in volume to 60 mL and water added (100 mL). The aqueous layer was extracted with EtOAc (6×100 mL). The combined organic extracts were washed with brine (100 mL), dried over $Na_2SO_4$ and concentrated to give 12.1 g of a yellow solid (aniline), which was used without further purification.

Step 3

To the above aniline (12.1 g, 49.9 mmol) in acetone (200 mL) and water (40 mL) was added $NaHCO_3$ (8.94 g, 106 mmol) and then benzylchloroformate (8.25 mL, 54.9 mmol). After stirring overnight, the mixture was poured into ice water (300 mL) and the resulting tan precipitate was collected on a filter, washed with water and dried in a vacuum oven to give the Cbz aniline derivative as a tan solid (16.9 g, 90% yield). mp=92–96° C. MS (M+1)=377 m/z.

Step 4

To the above Cbz aniline (0.920 g, 2.44 mmol) in THF (20 mL) at −78° C. was added n-BuLi (2.5 M, 1.00 mL, 2.5 mmol) dropwise. After stirring for 40 min, (R)-glycidyl butyrate (0.38 mL, 2.6 mmol) was added dropwise and the resulting mixture was allowed to warm to rt overnight. The mixture was concentrated and ether added (40 mL). The resulting solid was collected on a filter, washed with ether (100 mL) and water (3×100 mL). After drying in a vacuum oven (50° C.) Compound 1 was isolated as a tan solid (0.37 g, 44% yield). mp=117–119° C. MS (M+1)=343 m/z.

EXAMPLE 2

Acetamide, N-[[(5S)-3-[4-(3,4-dihydro-2(1H)-isoquinolinyl)-3-fluorophenyl]-2-oxo-5-oxazolidinyl]methyl]-

Compound 2

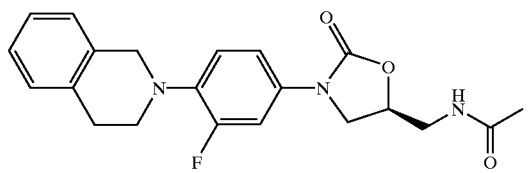

Step 1

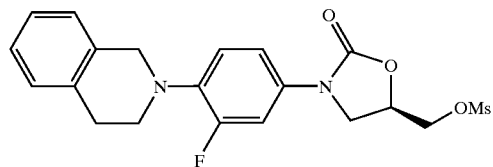

To the oxazolidinone carbinol from Example 1 (0.246 g, 0.718 mmol), in CH$_2$Cl$_2$ (10 mL) at 0° C. was added triethylamine (0.30 mL, 2.2 mmol) and, after 10 min, methanesulfonyl chloride (0.08 mL, 1.03 mmol). After allowing the reaction mixture to warm to rt over 1 hr the mixture was poured into water (30 mL) and extracted with CH$_2$Cl$_2$ (6×20 mL). The combined organic extracts were washed with brine (30 mL), dried over Na$_2$SO$_4$, concentrated and used without further purification. MS (M+1)=421 m/z.

Step 2

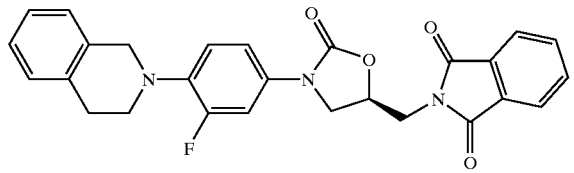

To the mesylate from Example 2 (~0.72 mmol) in DMF (10 mL) was added potassium phthalimide (0.30 g, 1.6 mmol) and the reaction mixture was heated to 90° C. for 12 hrs. After cooling to rt water was added and a ppt collected on a filter, washed with water (100 mL), and dried in a vacuum oven (50° C.) to provide 0.26 g of a tan solid (76% yield for two steps). mp=166–169° C. MS (M+1)=471 m/z.

Step 3

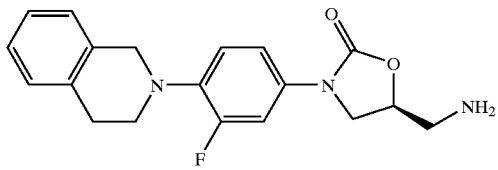

To the phthalimide from Example 3 (0.215 g, 0.457 mmol) in MeOH (6 mL) was added hydrazine hydrate (100 µL, 2.06 mmol) and the mixture heated to reflux overnight. After cooling to rt the reaction mixture was concentrated and the residue taken up in CH$_2$Cl$_2$, filtered and concentrated. A tan solid (0.15 g, 99% yield) was obtained and used without further purification. MS (M+1)=342 m/z.

Step 4

To the amine (0.15 g, 1.4 mmol) in CH$_2$Cl$_2$ was added pyridine (45 µL, 0.56 mmol) and then Ac$_2$O (100 µL, 1.04 mmol). After stirring for 2 hrs the mixture was poured into water, extracted with CH$_2$Cl$_2$ (6×10 mL), and the organic extracts were concentrated and chromatographed on silica with 5% MeOH/CH$_2$Cl$_2$ as eluent to give Compound 2 as a white solid (0.14 g, 83%). mp=131–134° C. MS (M+1)=384 m/z.

EXAMPLE 3

Acetamide, N-[[(5S)-3-[4-(3,4-dihydro-2,7-naphthyridin-2(1H)-yl)-3-fluorophenyl]-2-oxo-5-oxazolidinyl]methyl]-

Compound 3

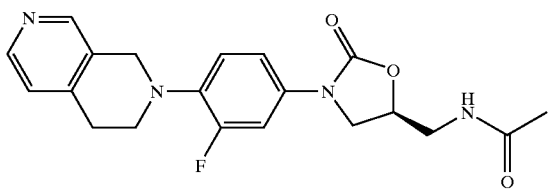

Step 1

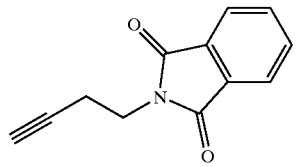

N-But-3-ynylphthalimide

The title compound was prepared according to the procedure of Iyer and Liebeskind (*J. Amer. Chem. Soc*, 1987, 109, 2759–2770) via a Mitsunobu reaction between phthalimide and 3-butyn-1-ol in 84% yield. The product was isolated as white crystals. mp=137–139° C. (lit. mp=136–137° C.).

Step 2

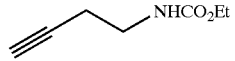

N-(Ethoxycarbonyl)but-3-ynylamine

The alkylated phthalimide from Step 1 (65.51 mmol) and hydrazine hydrate (72.15 mmol) in ethanol (350 mL) were stirred at room temperature for 3 days. After cooling to 0° C., triethylamine (89.68 mmol) was added followed by ethyl chloroformate (86.80 mmol). The reaction was warmed to room temperature and stirred overnight. A solid formed and was filtered off and the remaining alcoholic filtrate evaporated. The residue was dissolved in ether (1 L) and washed with several portions of water. The ethereal layer was dried over MgSO$_4$, filtered, concentrated and the residue subjected to chromatography on silica gel with 10% EtOAc/hexanes as the eluent to provide an oil. $^1$H NMR (CDCl$_3$) δ 5.00(br s, 1H), 4.15 (m, 2H), 3.32 (m, 2H), 2.49 (m, 2H), 2.01 (m, 1H), 1.23 (m, 3H).

Step 3

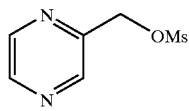

Pyrazin-2-ylmethanol was prepared as described by Piera and Seoane (*Anales de Quimica*, 1979, 75, 899–903). To pyrazin-2-ylmethanol (12.80 mmol) and triethylamine (20.08 mmol) in CH$_2$Cl$_2$ (80 mL) at 0° C. was added methanesulfonyl chloride (15.50 mmol). After stirring at 0° C. for 45 min, the reaction was rapidly washed with cold water (50 mL), aqueous NaHCO$_3$ (50 mL), dried (MgSO$_4$) and filtered. Toluene (25 mL) was added to the organic filtrate and the CH$_2$Cl$_2$ evaporated. The mesylate, as a solution in toluene, was used immediately in the next reaction since the compound rapidly decomposes.

Step 4

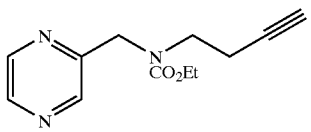

To the carbamate from Step 2 (10.41 mmols) in toluene (25 mL) at rt was added powdered KOH (48.11 mmol) and ca. 150 mg benzyltriethylammonium chloride. To this mixture was added the toluene solution of mesylate from Step 3 (assume 12.80 mmol) dropwise over a period of 30 min. The reaction was stirred at rt overnight. The mixture was filtered, washing with toluene, and the filtrate concentrated and chromatographed on silica using 40% EtOAc/hexanes to 60% EtOAc/hexanes as eluent. The product was obtained as a yellow liquid (54% yield). The NMR showed a mixture of rotamers. $^1$H NMR (CDCl$_3$) δ 8.45–8.70 (m, 3H), 4.70 (s, 2H), 4.11–4.30 (m, 2H), 3.50–3.68 (m, 2H), 2.45–2.58 (m, 2H), 1.98–2.01 (m, 1H), 1.18–1.410 (m, 3H).

Step 5

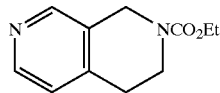

N-(Ethoxycarbonyl)-N-(but-3-ynyl)-aminomethylpyrazine (15.90 mmol) in trifluoroacetic acid (30 mL) was heated at reflux for 40 hr. After cooling, the reaction was carefully poured into water (300 mL) and made basic with K$_2$CO$_3$(s). This was extracted with CH$_2$Cl$_2$ (4×100 mL). The combined organic layers were dried (MgSO$_4$), filtered and evaporated. The compound was isolated as a gold oil after silica gel chromatography using 70% EtOAc/hexanes to 15% MeOH/EtOAc as the eluent. MS=207 (M+1). $^1$H NMR (CDCl$_3$) δ 8.32–8.42 (m, 2H), 7.07 (d, J=5.0 Hz, 1H), 4.67 (s, 2H), 4.20 (q, J=8.6 Hz, 2H), 3.72 (br t, J=5.1 Hz, 2H), 2.87 (br t, J=5.1 Hz, 2H), 1.30 (t, J=8.6 Hz, 3H). IR (KBr) 1699 cm$^{-1}$. Anal. Calcd. for C$_{11}$H$_{14}$N$_2$O$_2$/0.5 H$_2$O: C, 61.38; H, 7.02; N, 13.01. Found: C, 61.63; H, 6.66; N, 13.26.

Step 6

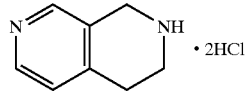

The above Diels-Alder adduct from Step 5 (8.73 mmol) and concentrated hydrochloric acid (20 mL) were heated at reflux for 22 hr. After cooling, the solvent was evaporated and the resulting solid triturated with acetone to give the dihydrochloride salt as a dark brown solid (90% yield). MS=135 (M+1).

Step 7

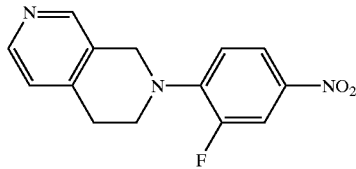

To the dihydrochloride salt from Step 6 (7.57 mmol) and 3,4-difluoronitrobenzene (7.59 mmol) in DMF (20 mL) at 80° C. was added diisopropylethylamine (24.1 mmol) in DMF (40 mL) dropwise over 1.5 hrs. Heating was continued overnight. After cooling, the reaction was added to water (650 mL) with stirring. The resulting solid was collected by filtration, washed with water and dried to give the product as a mustard-colored solid (69% yield). MS=274 (M+1); mp=142–143° C. $^1$H NMR (CDCl$_3$) δ 8.41–8.43 (m, 2H), 8.02 (dd, J=8.9, 2.5 Hz, 1H), 7.96 (dd, J=13.1 Hz, 2.7 Hz, 1H), 7.12 (d, J=5.0 Hz, 1H), 7.00 (t, J=8.9 Hz, 1H), 4.53 (s, 2H), 3.68 (t, J=5.8 Hz, 2H), 3.03 (t, J=5.8 Hz, 2H). IR (KBr) 1600, 1516, 1336 cm$^{-1}$. Anal. Calcd. for: C$_{14}$H$_{12}$FN$_3$O$_2$/0.4H$_2$O: C, 59.95; H, 4.60; N, 14.98. Found: C, 60.02; H, 4.27; N, 14.89.

Step 8

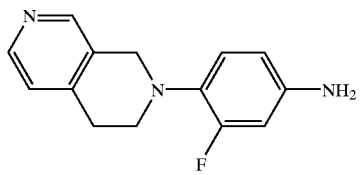

The nitro compound from Step 7 (5.23 mmol) and tin (II) chloride (14.29 mmol) in ethanol (60 mL) were heated at reflux for 38 hrs. After cooling, the reaction was poured into 1N NaOH (250 mL) and extracted with CH$_2$Cl$_2$ (3×100 mL). The combined organic layers were washed with water, dried over MgSO$_4$, filtered and evaporated to afford a quantitative yield of the crude aniline derivative. $^1$H NMR (CDCl$_3$) δ8.34–8.44 (m, 2H), 7.07 (d, J=5.0 Hz, 1H), 6.88 (t, J=8.9 Hz, 1H), 6.40–6.49 (m, 2H), 4.18 (s, 2H), 3.60 (br s, 2H), 3.30 (t, J=5.8 Hz, 2.98 (t, J=5.8 Hz, 2H).

Step 9

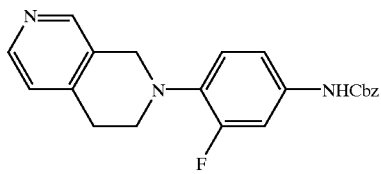

To the crude aniline derivative from Step 8 (5.23 mmol) and NaHCO$_3$ (12.02 mmol) in acetone (100 mL) and water (50 mL) at 0° C. was added benzyl chloroformate (5.74 mmols). The reaction was warmed to rt and stirred overnight. The mixture was poured into ice water (500 mL) with stirring and the resulting solid collected, washed with water and dried. The product was isolated as a tan solid (86% yield). MS=378 (M+1). $^1$H NMR (CDCl$_3$) δ 8.37 (m, 2H), 7.33–7.41 (m, 6H), 7.07 (d, J=5.0 Hz, 1H), 6.92–7.00 (m, 2H), 6.65 (br s, 1H), 5.20 (s, 2H), 4.25 (s, 2H), 3.38 (t, J=5.8 Hz, 2H), 2.98 (t, J=5.8 Hz, 2H).

Step 10

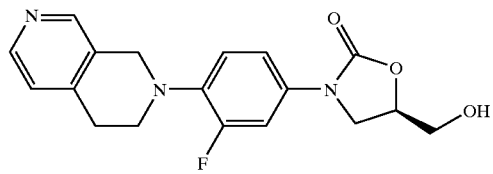

To the Cbz derivative from Step 9 (1.72 mmol) in THF (40 mL) at −78° C. was added n-BuLi (2.5M in hexanes, 2.5 mmol) and the mixture was stirred for 20 min. (R)-Glycidyl butyrate (2.54 mmol) was added and the reaction warmed to rt. After stirring overnight, the mixture was poured into sat. aqueous ammonium chloride (100 mL) and extracted with EtOAc (3×100 mL). The combined organic layers were washed with water, dried over MgSO$_4$, filtered, concentrated and chromatographed on silica with 5% MeOH/chloroform as eluent. The product was isolated as a cream-colored powder (44% yield). MS=344 (M+1). $^1$H NMR (CDCl$_3$/DMSO-d$_6$) δ 8.36–8.38 (m, 2H), 7.53 (dd, J=14.3, 2.6 Hz, 1H), 7.08–7.16 (m, 2H), 7.02 (t, J=9.1 Hz, 1H), 4.68–4.76 (m, 1H), 4.27 (s, 2H), 4.08–4.26 (m, 2H), 4.00 (d, J=7.8 Hz, 2H), 3.90–3.94 (m, 1H), 3.72–3.77 (m, 1H), 3.41 (t, J=5.8 Hz, 2H), 2.99 (t, J=5.8 Hz, 2H).

Step 11

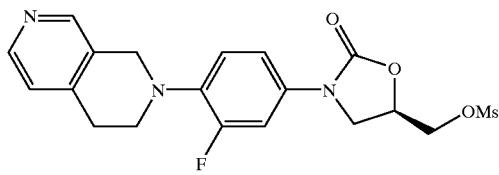

To the alcohol from Step 10 (0.757 mmol) in CH$_2$Cl$_2$ (50 mL) at 0° C. was added triethylamine (0.932 mmol) and methanesulfonyl chloride (0.904 mmol). The reaction was stirred at 0° C. for 2 hr, warmed to rt and stirred overnight. The mixture was poured into water (75 mL) and the layers separated. The aqueous layer was extracted with additional CH$_2$Cl$_2$ (2×100 mL). The combined organic layers were dried over MgSO$_4$, filtered and evaporated to afford crude mesylate as a brown-yellow oil. MS=422 (M+1).

Step 12

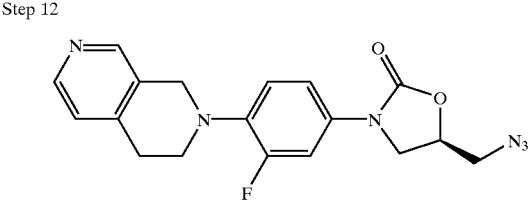

Crude mesylate from Step 11 (0.757 mmol) and sodium azide (3.92 mmol) in DMF (35 mL) were heated at 75° C. overnight. After cooling, the reaction was poured into water (200 mL) with stirring. The aqueous layer was extracted with EtOAc (2×100 mL). The combined organic layers were washed with water (2×100 mL), dried over MgSO$_4$, filtered and evaporated to afford the azide as a brown semi-solid. MS=369 (M+1). $^1$H NMR (CDCl$_3$) δ 8.31–7.45 (m, 2H), 7.49 (dd, J=14.2, 2.6 Hz, 1H), 7.07–7.19 (m, 2H), 7.00 (t, J=9.0 Hz, 1H), 4.71–4.86 (m, 1H), 4.28 (s, 2H), 4.08 (t, J=9.6 Hz, 1H), 3.85 (dd, J=9.6, 5.8 Hz, 1H), 3.71 (dd, J=17.0, 4.1 Hz, 1H), 3.60 (dd, J=17.0, 4.0 Hz, 1H), 3.42 (t, J=5.8 Hz, 2H), 2.99 (t, J=5.8 Hz, 2H).

Step 13

Crude azide from Step 12 (0.757 mmol) and triphenylphosphine (0.815 mmol) in THF (20 mL) were stirred at rt overnight. An aliquot showed MS=603 (M+1) for the iminophosphorane intermediate. Water (0.85 mL) was added and the reaction heated at 80° C. for 4 hr. The volatiles were evaporated and the water removed by azeotroping with several portions of benzene to afford the crude amine. MS=343 (M+1). The crude amine was dissolved in THF (20 mL), and acetic anhydride (0.954 mmol) and pyridine (1.11 mmols) were added. The reaction was stirred at rt overnight. The reaction was poured into water (50 mL) and extracted with EtOAc (3×100 mL). The combined organic layers were washed with water, dried over MgSO$_4$, filtered, concentrated and chromatographed on silica with 5% MeOH/CH$_2$Cl$_2$ as the eluent to provide Compound 3 as a yellow solid. mp=141–144° C. (decomp). MS=385 (M+1). $^1$H NMR (CDCl$_3$) δ 8.36–8.39 (m, 2H), 7.48 (dd, J=14.0, 2.4 Hz, 1H), 7.08–7.16 (m, 2H), 7.01 (t, J=8.9 Hz, 1H), 6.14 (br t, J=6.0 Hz, 1H), 4.74–4.82 (m, 1H), 4.28 (s, 2H), 4.04 (t, J=9.0 Hz, 1H), 3.57–3.79 (m, 3H), 3.41 (t, J=5.7 Hz, 2H), 2.99 (t, J=5.7 Hz, 2H).

EXAMPLE 4

Acetamide, N-[[(5S)-3-[4-(3,4-dihydro-1-naphthyridin-2(1H)-yl)-3-fluorophenyl]-2-oxo-5-oxazolidinyl]methyl]-

Compound 4

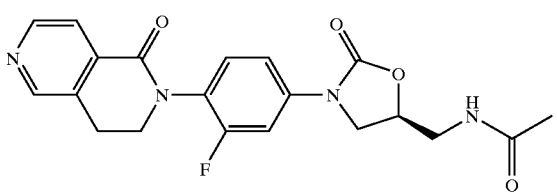

Step 1

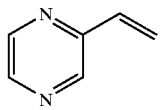

2-Vinyl pyrazine was synthesized according to the procedures described by Kamal, M.; Neubert, M.; and Levine, R. *J. Org. Chem.*, 1962, 27, 1363.

Step 2

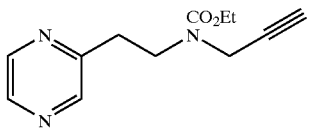

2-(2-(N-carboethoxypropargyl)amino)pyrazine was prepared in the manner of Sahu, D. P. *Indian J. Chem. Sec B*, 1998, 37, 1149 except that propargyl amine was employed in place of ethylamine.

Step 3

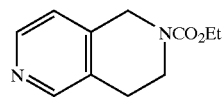

N-ethoxycarbonyl-N-propargyl-2-aminoethylpyrazine (0.6776 g, 2.906 mmol) in trifluoroacetic acid (20 mL) was refluxed for 72 hrs. The reaction was poured into water (30 mL), made basic with $K_2CO_3$(s), and extracted with $CH_2Cl_2$ (6×20 mL). The organic solutions were dried over $Na_2SO_4$, concentrated and chromatographed on silica eluting with 2% MeOH/$CH_2Cl_2$, to afford the desired product (0.2416 g, 40% yield). MS=206.9 (M+1)

Step 4

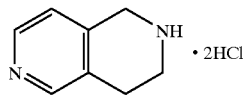

The above carbamate (0.2416 g, 1.171 mmol) was suspended in concentrated HCl (10 mL) and refluxed for 20 hrs. The mixture was concentrated and the residue was triturated with acetone to afford the di-HCl salt as a brown solid (0.1416 g, 60% yield). MS=134.9 (M+1)

Step 5

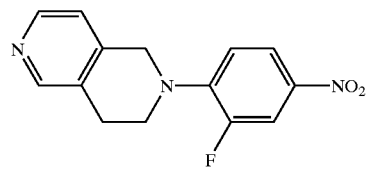

To the above di-HCl salt (1.656 g, 7.998 mmol) in DMF (10 mL) was added 3,4-difluoronitrobenzene and the solution was heated to 60° C. At this time, diisopropylethylamine was added dropwise over 3 hrs. The heating was continued for 20 hrs. The solution was poured into water (10 mL), and extracted with EtOAc (6×15 mL). The combined organic extracts were washed with water (20 mL), brine (20 mL), and dried over $Na_2SO_4$. Filtration and concentration of the solution afforded a dark orange oil. Trituration of the oil with hexanes afforded the product as a bright yellow solid (0.987 g, 40% yield). MS=273.9 (M+1)

Step 6

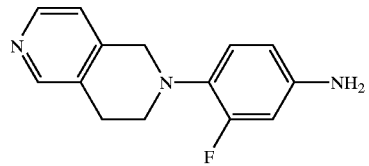

The nitro compound from Step 5 (0.807 g, 2.95 mmol) was dissolved in MeOH (80 mL) and degassed (by bubbling nitrogen through the solution for 20 min). To this mixture was added ammonium formate (0.931 g, 14.8 mmol), followed by 10% Pd/C (50 mg). The mixture was heated to 50° C. for 20 hours whereupon an additional amount of ammonium formate (0.400 g, 6.36 mmol) and 10% Pd/C (30 mg) was added. After an additional 6 hrs the reaction was cooled to rt and filtered through a Celite pad, eluting with MeOH (800 mL). The filtrate was concentrated to provide a tan residue (0.690 g, 96% yield). MS=244.0 (M+1)

Step 7

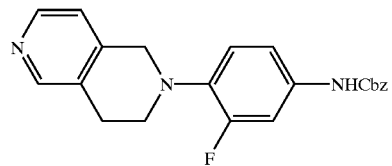

To the aniline (0.690 g, 2.84 mmol) in acetone (40 mL) and water (20 mL) was added $NaHCO_3$ (1.00 g, 11.9 mmol). The mixture was cooled to 0° C. and benzyl chloroformate (0.43 mL, 3.0 mmol) was added dropwise. The reaction was allowed to warm to rt and was stirred for 20 hrs whereupon acetone was removed under vacuum, and the reaction diluted with water (40 mL). The solution was extracted with EtOAc (6×30 mL), dried over $Na_2SO_4$, concentrated to a reddish liquid and chromatographed on silica with 1% MeOH/EtOAc followed by 2% MeOH/EtOAc as eluents to provide the product as an off-white solid (0.431 g, 40% yield). MS=378.0 (M+1)

Step 8

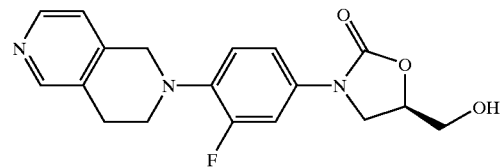

The above Cbz derivative (1.090 g, 2.884 mmol) in THF (80 mL) was cooled to −78° C. and n-BuLi (1.6 mL, 4.0 mmol) added dropwise. The reaction was warmed to rt for 1 hr, then recooled to −78° C. whereupon (R)-glycidyl butyrate (0.54 mL, 4.0 mmols) was added. The reaction was allowed to warm to rt and stir over 20 hrs. After removing THF under vacuum the resulting residue was diluted with water (15 mL) and extracted with CH$_2$Cl$_2$ (6×15 mL). The organic layers were dried over Na$_2$SO$_4$, concentrated to a brown oil and the residue used without further purification. MS=344.0 (M+1)

Step 9

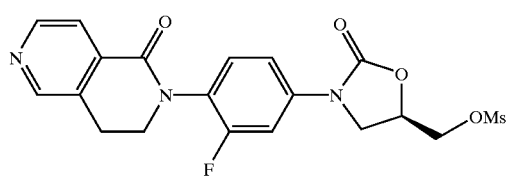

To the above crude alcohol (~2.8 mmol) in DMF (45 mL) was added triethylamine (0.80 mL, 5.76 mmol). After cooling to 0° C. methanesulfonyl chloride (0.313 mL, 4.04 mmol) was added dropwise and then the reaction was allowed to warm to rt. The mixture was poured into water (50 mL) and extracted with CH$_2$Cl$_2$ (6×50 mL). The combined organics were washed with water (4×80 mL) followed by brine (80 mL), and then dried over Na$_2$SO$_4$. Concentration of the organic solution provided a yellow residue which was used without further purification. MS=436.0 (M+1)

Step 10

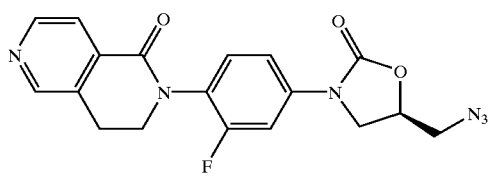

The above mesylate (~2.8 mmol) and sodium azide (0.700 g, 5.82 mmol) in DMF (100 mL) were heated to 75° C. After 6 hrs the mixture was cooled to rt, diluted with water (300 mL) and extracted with EtOAc (6×100 mL). The combined organic layers were washed with water (100 mL), brine (100 mL), and then dried over Na$_2$SO$_4$. Concentration of the filtrate provided a yellow oil which was chromatographed on silica with 1% MeOH/EtOAc followed by 5% MeOH/EtOAc as eluents to afford the azide (0.170 g, 16% yield for 3 steps). MS=383.0 (M+1)

Step 11

The azide from Step 10 (0.170 g, 0.445 mmol) was dissolved in EtOAc (30 mL) and degassed (by bubbling nitrogen through the solution for 20 min) whereupon 10% Pd/C (30 mg) was added. The mixture was shaken on a Parr apparatus under a hydrogen atmosphere (50 psi) for 24 hrs. Upon complete reduction (by MS), the flask was evacuated and then refilled with nitrogen. At this time, pyridine (0.22 mL, 2.67 mmol) and acetic anhydride (0.13 mL, 1.34 mmol) were added directly to the flask and the reaction allowed to stir for 4 hrs. Upon completion (by MS), the mixture was filtered through a Celite pad, eluting with MeOH (300 mL), concentrated and purified by column chromatography on silica using 5% MeOH/EtOAc followed by 10% MeOH/EtOAc as eluents to provide Compound 4 (0.050 g, 28% yield) as a white solid. MS=399.1 (M+1)

EXAMPLE 5

Acetamide, N-[[(5S)-3-[4-(7,8-dihydropyrido[4,3-d]pyrimidin-6(5H)-yl)-3-fluorophenyl]-2-oxo-5-oxazolidinyl]methyl]-

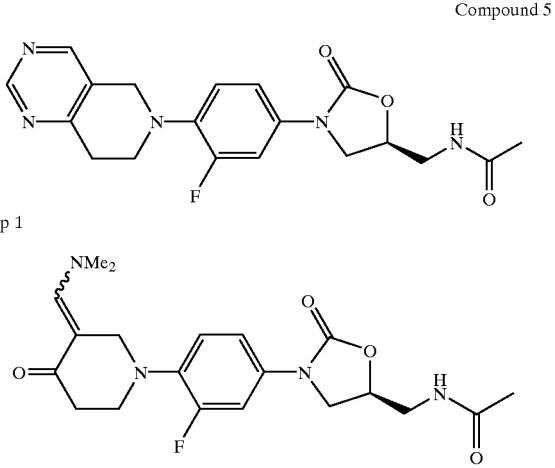

Compound 5

Step 1

To N-[(3-piperidinone-3-fluorophenyl) 5-oxazolidinyl]methyl acetamide (prepared according to WO95/25106 and WO96/13502)(0.54 g, 1.5 mmol) was added methoxy-bis (dimethylamino)methane (5 mL). After heating at 50° C. for 1 hr all volatiles were removed in vacuo to provide an orange solid. The crude β-ketoenamine was used without further purification.

Step 2

To the above crude β-ketoenamine (0.106 g, 0.262 mmol) was added benzene (3 mL), DMF (1 mL) and formamidine acetate (0.0420 g, 0.403 mmol). After heating overnight at reflux the reaction mixture was cooled to rt and water (8 mL) was added. A ppt formed and was collected by filtration, dried in a vacuum oven (50° C.), and chromatographed on silica with 5% MeOH/CH$_2$Cl$_2$ as eluent to afford Compound 5 as a yellow solid (0.0064 g, 6% yield). MS (M+1)=386 m/z.

EXAMPLE 6

Acetamide, N-[[(5S)-3-[4-(7,8-dihydro-2methylpyrido[-4,3-d]pyrimidin-6(5H)-yl)-3-fluorophenyl]-2-oxo-5-oxazolidinyl]methyl]-

Compound 6

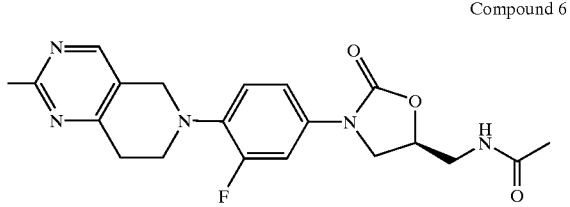

To the crude β-ketoenamine prepared as in Example 5, Step 1 (0.100 g, 0.247 mmol) was added EtOAc (3 mL), DMF (1 mL), acetamidine acetate (0.0374 g, 0.310 mmol) and K$_2$CO$_3$ (0.16 g, 1.2 mmol). After heating overnight at reflux the reaction mixture was cooled to rt and water (8 mL) added. A ppt formed and was collected on a filter, dried in a vacuum oven (50° C.), and chromatographed on silica with 5% MeOH/CH$_2$Cl$_2$ as eluent to afford the product as a light yellow solid (0.0081 g, 8% yield). mp=177–180° C. MS (M+1)=400 m/z.

EXAMPLE 7

Acetamide, N-[[(5S)-3-[4-(7,8-dihydro-2-(2-methyl-4-thiazolyl)pyrido[4,3-d]pyrimidin-6(5H)-yl)-3-fluorophenyl]-2-oxo-5-oxazolidinyl]methyl]-

Compound 7

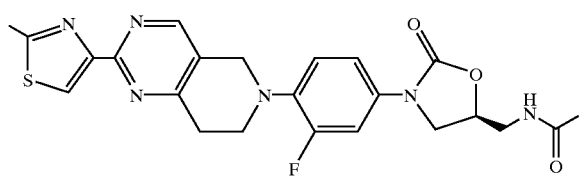

To the crude β-ketoenamine prepared as in Example 5, Step 1 (0.112 g, 0.278 mmol) was added benzene (5 mL), DMF (1 mL) and 2-methyl-5-amidinothiazole hydrochloride (0.0743 g, 0.418 mmol). After heating overnight at reflux the reaction mixture was cooled to rt and water (8 mL) was added. A ppt formed and was collected by filtration, dried in a vacuum oven (50° C.), and chromatographed on silica with 5% MeOH/CH$_2$Cl$_2$ as eluent to afford the product as a yellow solid (0.0100 g, 7% yield). MS (M+1)=483 m/z.

EXAMPLE 8

Acetamide, N-[[(5S)-3-[4-(7,8-dihydro-2-(4-pyridinyl)pyrido[4,3- d]pyrimidin-6(5H)-yl)-3-fluorophenyl]-2-oxo-5-oxazolidinyl]methyl]-

Compound 8

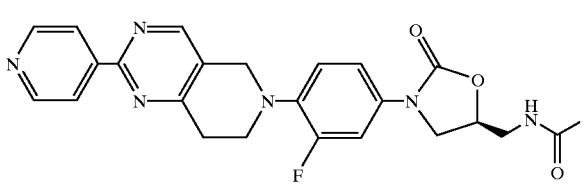

To the crude β-ketoenamine prepared as in Example 5, Step 1 (0.120 g, 0.278 mmol) was added benzene (5 mL), DMF (1 mL) and 4-pyridinoamidine hydrochloride (0.0721 g, 0.458 mmol). After heating overnight at reflux the reaction mixture was cooled to rt and water (8 mL) was added. A ppt formed and was collected by filtration, dried in a vacuum oven (50° C.), and chromatographed on silica with 5% MeOH/CH$_2$Cl$_2$ as eluent to afford the product as a light yellow solid (0.0049 g, 4% yield). MS (M+1)=463 m/z.

EXAMPLE 9

Acetamide, N-[[(5S)-3-[4-(7,8-dihydro-2-pyrazinylpyrido[4,3-d]pyrimidin-6(5H)-yl)-3-fluorophenyl]-2-oxo-5-oxazolidinyl]methyl]-

Compound 9

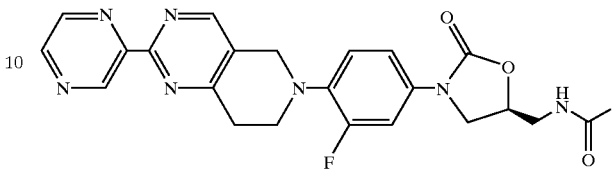

To the above crude β-ketoenamine (0.110 g, 0.278 mmol) was added benzene (5 mL), DMF (1 mL) and pyrazinoamidine hydrochloride (0.0660 g, 0.416 mmol). After heating overnight at reflux the reaction mixture was cooled to rt and water (8 mL) was added. A ppt formed and was collected by filtration, dried in a vacuum oven (50° C.), and chromatographed on silica with 5% MeOH/CH$_2$Cl$_2$ as eluent to afford the product as a yellow solid (0.0038 g, 3% yield). MS (M+1)=464 m/z.

EXAMPLE 10

Acetamide, N-[[(5S)-3-[3-fluoro-4-(1,4,6,7-tetrahydro-5H-pyrazolo[4,3- c]pyridin-5-yl)-3-phenyl]-2-oxo-5-oxazolidinyl]methyl]-

Compound 10

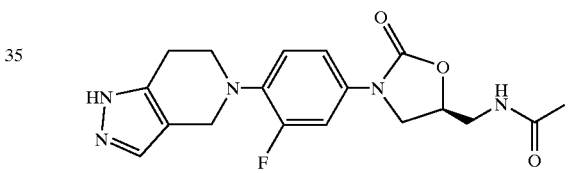

To the crude β-ketoenamine prepared as in Example 5, Step 1 (3.40 mmols) was added DMF (20 mL) and hydrazine hydrochloride (2.40 g, 35.0 mmols). After heating at 90° C. for 1 hr the reaction mixture was cooled to RT and water (60 mL) was added. A ppt formed and was collected by filtration and dried in a vacuum oven (50° C.). The crude solid was triturated with methanol to provide a tan solid (0.0449 g, 4% yield). Mp=108–110° C. MS (M+1)=374 m/z.

EXAMPLE 11

Acetamide, N-[[(5S)-3-[3-fluoro-4-(1,4,6,7-tetrahydro-1-methyl 5H-pyrazolo[4,3-c]pyridin-5-yl) phenyl]-2-oxo-5-oxazolidinyl]methyl]-

Compound 11

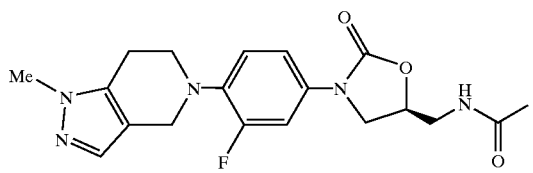

To the crude β-ketoenamine prepared as in Example 5, Step 1 (0.308 mmols) was added DMF (2 mL), methylhydrazine (0.24 mL, 4.5 mmols), and HCl in ether (4.4 mL, 1.0 M). After heating at 90° C. for 1 hr the reaction mixture was cooled to RT and water (60 mL) was added. A ppt formed and was collected by filtration and dried in a vacuum oven (50° C). The crude solid was chromatographed on silica with 5->10% MeOH/CH$_2$Cl$_2$ as eluent to afford a light yellow solid (0.0212 g, 6% yield). Mp=187–189° C. MS (M+1)= 388 m/z.

The invention has been described in detail with particular reference to the above embodiments thereof. The above embodiments and examples are given to illustrate the scope and spirit of the present invention. These embodiments and examples will make apparent, to those skilled in the art, other embodiments and examples. These other embodiments and examples are within the contemplation of the present invention. It will be understood that variations and modifications can be effected within the spirit and scope of the invention; therefore, the instant invention should be limited only by the appended claims.

We claim:

1. A compound of Formula I

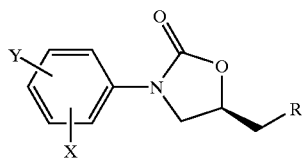

Formula I wherein

R is selected from the group consisting of OH, N$_3$, —OR$_1$, —O-aryl, —O-heteroaryl, —OSO$_2$R$_2$, —NR$_3$R$_4$, and

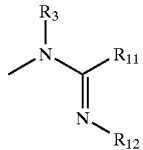

wherein (i) R$_1$ is benzyl or C$_{2-6}$-acyl;

(ii) R$_2$ is selected from the group consisting of phenyl, tolyl, and C$_{1-8}$-alkyl; and (iii) R$_3$ and R$_4$ are independently selected from the group consisting of hydrogen, C$_{3-6}$-cycloalkyl, phenyl, tert-butoxycarbonyl, fluorenyloxycarbonyl, benzyloxycarbonyl, —CO$_2$—R$_5$, —CO—R$_5$, —CO—SR$_5$, —CS—R$_5$, P(O)(OR$_6$)(OR$_7$), —SO$_2$—R$_8$ and C$_{1-6}$-alkyl optionally substituted with 1 to 3 members independently selected from the group consisting of C$_{1-5}$-alkoxycarbonyl, OH, cyano, and halogen, wherein R$_5$ is selected from the group consisting of hydrogen, C$_{3-6}$-cycloalkyl, trifluoromethyl, phenyl, benzyl, and C$_{1-6}$-alkyl optionally substituted with 1 to 3 members independently selected from the group consisting of C$_{1-5}$-alkoxycarbonyl, OH, cyano, halogen, and —NR$_9$R$_{10}$ in which R$_9$ and R$_{10}$ are independently selected from the group consisting of hydrogen, phenyl and C$_{1-4}$-alkyl;

R$_6$ and R$_7$ are independently hydrogen or C$_{1-4}$-alkyl; and

R$_8$ is phenyl or C$_{1-4}$-alkyl;

R$_{11}$ is selected from the group consisting of hydrogen, alkyl, —OR$_{13}$, —SR$_{13}$, amino, —NR$_{13}$R$_{14}$, aryl (C$_{1-8}$)alkyl, and mono-, di-, tri-, or per-halo C$_{1-8}$-alkyl;

R$_{12}$ is selected from the group consisting of CN, —COR$_{13}$, —COOR$_{13}$, —CO—NR$_{13}$R$_{14}$, —SO$_2$R$_{13}$, —SO$_2$—NR$_{13}$R$_{14}$, and nitro; and R$_{13}$ and R$_{14}$ are independently selected from the group consisting of hydrogen, alkyl, and aryl, or R$_{13}$ and R$_{14}$ taken together with the nitrogen atom to which they are attached form an unsubstituted or substituted pyrrolidinyl, piperidinyl, morpholinyl, thiomorpholinyl, or piperazinyl group;

X is 0 to 4 members independently selected from the group consisting of halogen, OH, mercapto, nitro, halo-C$_{1-8}$-alkyl, C$_{1-8}$-alkoxy, C$_{1-8}$-alkylthio, C$_{1-8}$-alkyl-amino, di(C$_{1-8}$-alkyl)amino, formyl, carboxy, alkoxycarbonyl, C$_{1-8}$ alkyl-CO—O—, C$_{1-8}$ alkyl-CO—NH—, carboxamide, aryl, heteroaryl, CN, amino, C$_{3-6}$-cycloalkyl, C$_{1-8}$-alkyl optionally substituted with one or more members selected from the group consisting of F, Cl, OH, C$_{1-8}$ alkoxy and C$_{1-8}$ acyloxy; and Y is a radical of Formula II:

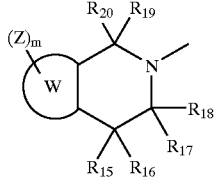

Formula II wherein

R$_{15}$, R$_{16}$, R$_{17}$, R$_{18}$, R$_{19}$, and R$_{20}$ are each independently selected from the group consisting of hydrogen, CN, nitro, C$_{1-8}$-alkyl, halo-C$_{1-8}$-alkyl, formyl, carboxy, alkoxycarbonyl, carboxamide, aryl, and heteroaryl, or R$_{15}$ and R$_{16}$ and/or R$_{17}$ and R$_{18}$ and/or R$_{19}$ and R$_{20}$ together form an oxo group;

the moiety W represents any five- to ten-membered aromatic or heteroaromatic ring, said heteroaromatic ring having 1 to 4 members selected from the group consisting of S, O, and N;

Z is selected from the group consisting of hydrogen, halogen, amino, alkyl, cycloalkyl, aryl, heteroaryl, heterocyclyl, CN, CHO, alkyl-CO—, alkoxy, (C$_{1-8}$-alkyl)-CONH—, and R$_{21}$R$_{22}$N-alkyl- wherein R$_{21}$ and R$_{22}$ are independently selected from the group consisting of hydrogen, C$_{1-6}$-alkyl, benzyl, aryl, and heteroaryl, or R$_{21}$ and R$_{22}$ together with the nitrogen to which they are attached form an unsubstituted or substituted pyrrolidinyl, piperidinyl, morpholinyl, thiomorpholinyl, or piperazinyl group; and m is 0 or 1 and the pharmaceutically acceptable salts and esters thereof.

2. The compound of claim 1 wherein X is halogen.

3. The compound of claim 1 wherein Z is selected from the group consisting of hydrogen, alkyl, aryl, and heteroaryl.

4. The compound of claim 1 wherein the moiety W is a fused phenyl ring or a five- or six-membered heteroaromatic ring having 1 to 4 members selected from the group consisting of S, O, and N.

5. The compound of claim 1 wherein Y is selected from the group consisting of

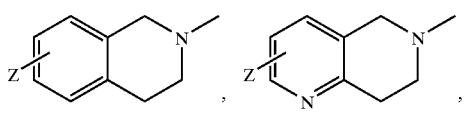

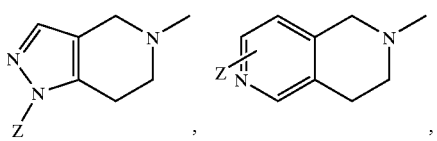

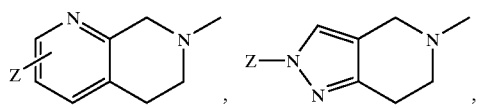

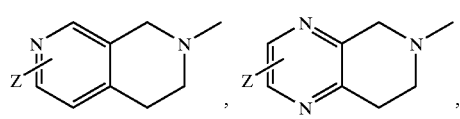

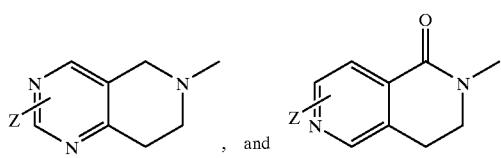

, and wherein

Z is selected from the group consisting of hydrogen, alkyl, aryl, heteroaryl, alkyl-CO—, and $R_{21}R_{22}N$-alkyl- wherein $R_{21}$ and $R_{22}$ are independently selected from the group consisting of hydrogen, $C_{1-6}$-alkyl, benzyl, aryl, and heteroaryl, or $R_{21}$ and $R_{22}$ together with the nitrogen atom to which they are attached form an unsubstituted or substituted pyrrolidinyl, piperidinyl, morpholinyl, thiomorpholinyl, or piperazinyl group.

6. The compound of claim 5 wherein X is halogen and Z is selected from the group consisting of hydrogen, alkyl, aryl, and heteroaryl.

7. The compound of claim 1 wherein R is selected from the group consisting of

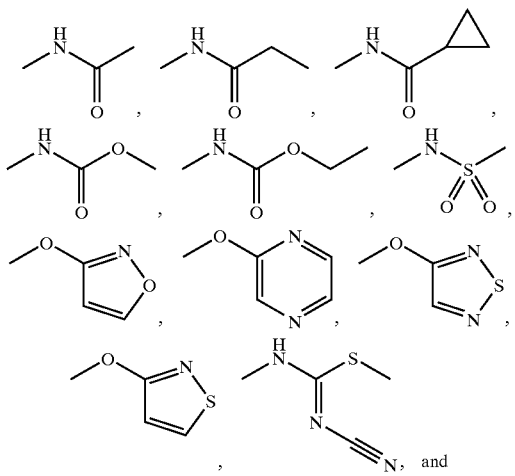

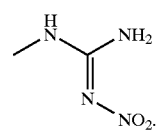

8. The compound of claim 6 wherein X is halogen and Z is selected from the group consisting of hydrogen, alkyl, aryl, and heteroaryl.

9. A compound of claim 1 having the formula:

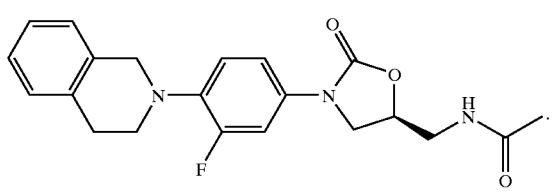

10. A compound of claim 1 having the formula:

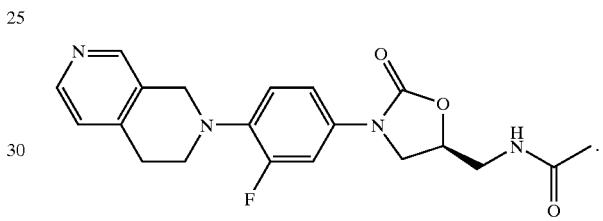

11. A compound of claim 1 having the formula:

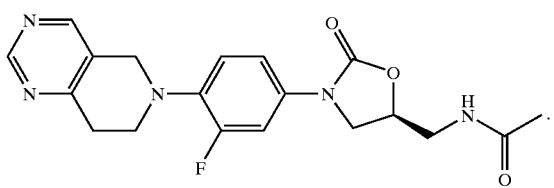

12. A compound of claim 1 having the formula:

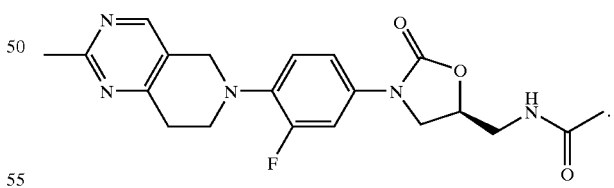

13. A compound of claim 1 having the formula:

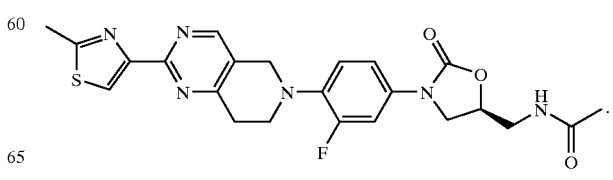

14. A compound of claim 1 having the formula:

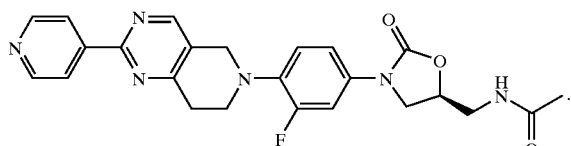

15. A compound of claim 1 having the formula:

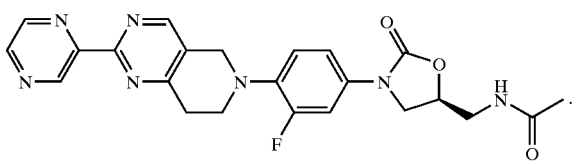

16. A compound of claim 1 having the formula:

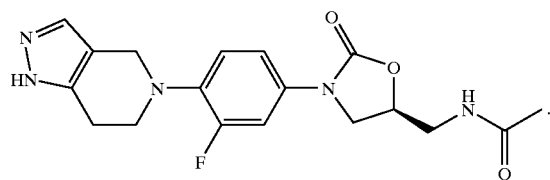

17. A compound of claim 1 having the formula:

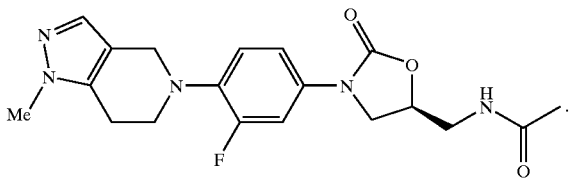

18. A pharmaceutical composition comprising a compound according to claim 1 and a pharmaceutically acceptable carrier.

19. A method of treating a subject having a condition selected from the group consisting of community-acquired pneumonia, upper and lower respiratory tract infections, skin and soft tissue infections, bone and joint infections and hospital-acquired lung infections, said method comprising the step of administering to the subject a therapeutically effective amount of a compound according to claim 1.

20. The method of claim 19 wherein said condition is caused by or contributed to by a bacterium selected from the group consisting of *S. aureus, S. epidermidis, S. pneumoniae, S. pyogenes, Enterococcus* spp., *Moraxella catarrhalis* and *H. influenzae*.

21. The method of claim 19 wherein said condition is caused by or contributed to by a bacterium that is a Gram-positive coccus.

22. The method of claim 21 wherein said Gram-positive coccus is drug-resistant.

* * * * *